United States Patent
Markison et al.

(10) Patent No.: US 10,653,337 B2
(45) Date of Patent: May 19, 2020

(54) LOCAL OBJECT DETECTION SYSTEM

(71) Applicants: Timothy W. Markison, Mesa, AZ (US); Sayfe Kiaei, Fountain Hills, AZ (US); Gary McCoy, Gilbert, AZ (US)

(72) Inventors: Timothy W. Markison, Mesa, AZ (US); Sayfe Kiaei, Fountain Hills, AZ (US); Gary McCoy, Gilbert, AZ (US)

( * ) Notice: Subject to any disclaimer, the term of this patent is extended or adjusted under 35 U.S.C. 154(b) by 221 days.

(21) Appl. No.: 15/680,863

(22) Filed: Aug. 18, 2017

(65) Prior Publication Data

US 2018/0052228 A1 Feb. 22, 2018

Related U.S. Application Data

(60) Provisional application No. 62/376,555, filed on Aug. 18, 2016.

(51) Int. Cl.
*A61B 5/103* (2006.01)
*G01S 13/88* (2006.01)
(Continued)

(52) U.S. Cl.
CPC .......... *A61B 5/1036* (2013.01); *A43B 3/0005* (2013.01); *A61B 5/002* (2013.01);
(Continued)

(58) Field of Classification Search
CPC ...... G01S 13/003; G01S 13/426; G01S 11/04; G01S 7/412; G01S 7/415; G01S 13/46
See application file for complete search history.

(56) References Cited

U.S. PATENT DOCUMENTS 3,184,739 A * 5/1965 Frederick ................ G01S 13/46
342/126
3,795,911 A * 3/1974 Hammack ............... G01S 13/58
342/106
(Continued)

OTHER PUBLICATIONS

"F-Scan System." Tekscan, Inc. https://www.tekscan.com/products-solutions/systems/f-scan-system. Accessed Aug. 18, 2017.
(Continued)

*Primary Examiner* — Bernarr E Gregory
(74) *Attorney, Agent, or Firm* — Garlick & Markison; Timothy W. Markison

(57) ABSTRACT

A method includes transmitting one or more local transmit radar signals and receiving a plurality of local receive radar signals that corresponds to the one or more local transmit radar signals being reflected or refracted off an object. The method further includes processing the plurality of local receive radar signals to determine a relative position of the object. The method further includes determining whether the object is positioned within a desired detection volume associated with a position of the transmitter section. When the object is positioned within the desired detection volume, further processing the local receive radar signals to determine movement pattern of the object and whether the movement pattern of the object is within a range of plausible movements for the object. When the movement pattern of the object is within a range of plausible movements for the object, tracking movement of the object within the desired detection volume.

12 Claims, 18 Drawing Sheets

(51) Int. Cl.

| | |
|---|---|
| *G01S 13/72* | (2006.01) |
| *G01S 13/58* | (2006.01) |
| *G01S 13/46* | (2006.01) |
| *G01S 13/42* | (2006.01) |
| *H04Q 9/00* | (2006.01) |
| *A63B 71/06* | (2006.01) |
| *A63B 24/00* | (2006.01) |
| *A61B 5/00* | (2006.01) |
| *A61B 5/16* | (2006.01) |
| *A61B 5/0205* | (2006.01) |
| *A61B 5/11* | (2006.01) |
| *A43B 3/00* | (2006.01) |
| *A61B 5/08* | (2006.01) |
| *A61B 5/024* | (2006.01) |
| *G01S 13/00* | (2006.01) |

(52) U.S. Cl.
CPC ........ *A61B 5/02055* (2013.01); *A61B 5/1118* (2013.01); *A61B 5/16* (2013.01); *A61B 5/6802* (2013.01); *A61B 5/7275* (2013.01); *A61B 5/743* (2013.01); *A63B 24/0062* (2013.01); *A63B 71/06* (2013.01); *G01S 13/42* (2013.01); *G01S 13/46* (2013.01); *G01S 13/58* (2013.01); *G01S 13/726* (2013.01); *G01S 13/88* (2013.01); *H04Q 9/00* (2013.01); *A61B 5/024* (2013.01); *A61B 5/0816* (2013.01); *A61B 2560/0214* (2013.01); *A61B 2562/0219* (2013.01); *G01S 2013/468* (2013.01); *H04Q 2209/40* (2013.01); *H04Q 2209/84* (2013.01); *H04Q 2209/845* (2013.01)

(56) References Cited

U.S. PATENT DOCUMENTS

| | | | | |
|---|---|---|---|---|
| 3,953,856 | A * | 4/1976 | Hammack | G01S 13/58 342/458 |
| 4,992,797 | A * | 2/1991 | Gjessing | G01S 7/412 342/190 |
| 5,247,307 | A * | 9/1993 | Gandar | G01S 7/415 342/192 |
| 5,410,314 | A * | 4/1995 | Frush | G01S 13/003 342/26 D |
| 6,222,481 | B1 * | 4/2001 | Abrahamson | G01S 7/412 342/90 |
| 7,394,046 | B2 * | 7/2008 | Olsson | G01S 11/04 244/3.1 |
| 2011/0267219 | A1 * | 11/2011 | Kisliansky | G01S 13/426 342/90 |

OTHER PUBLICATIONS

Munk-Stander, Jacob. "Evaluation of Piezoelectric Film Sensors for In-Shoe Pressure Measurement." Technical Report No. 06/04. Dept. of Computer Science, University of Copenhagen, Denmark. Feb. 16, 2006. 21 pages.

* cited by examiner

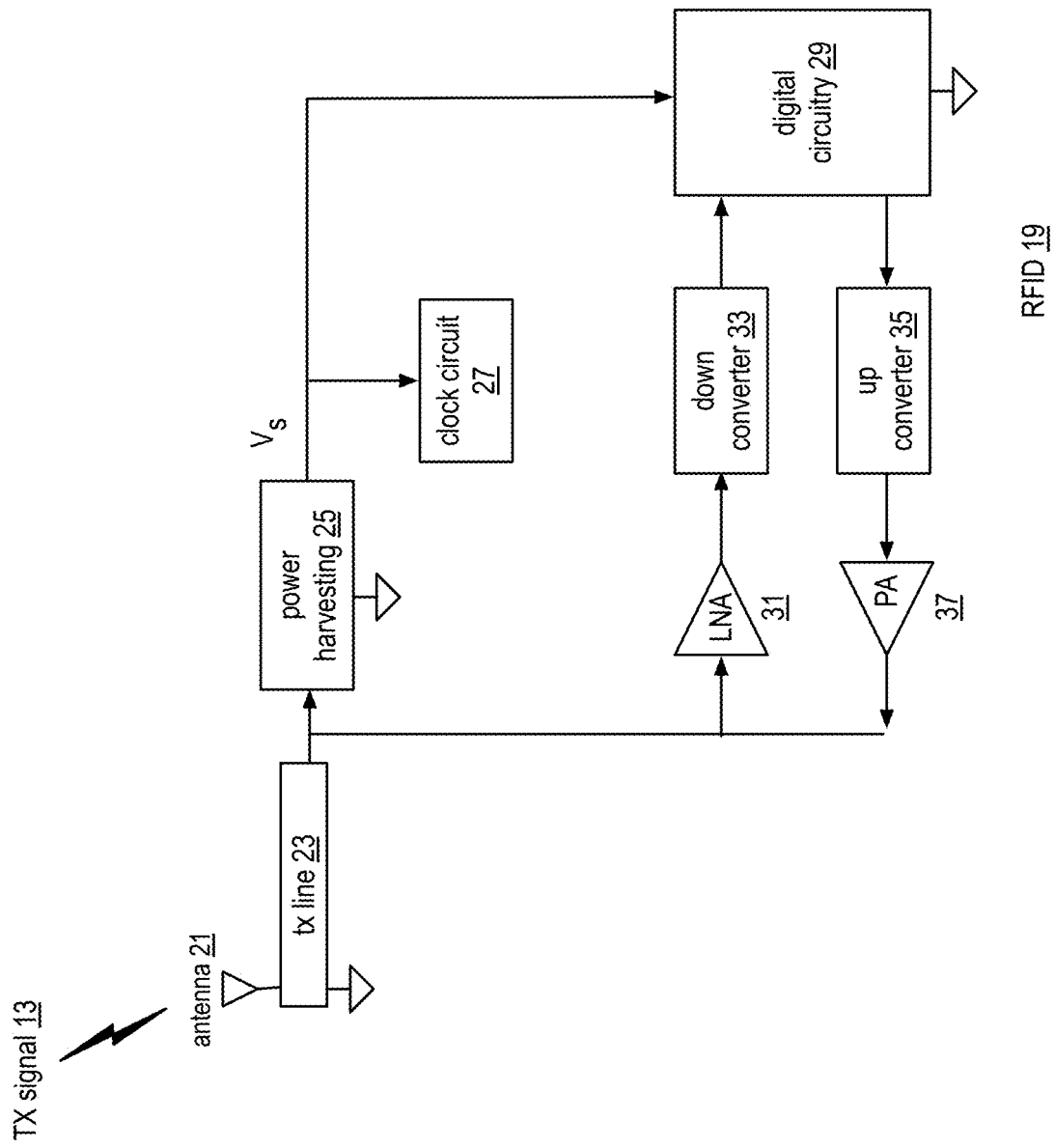

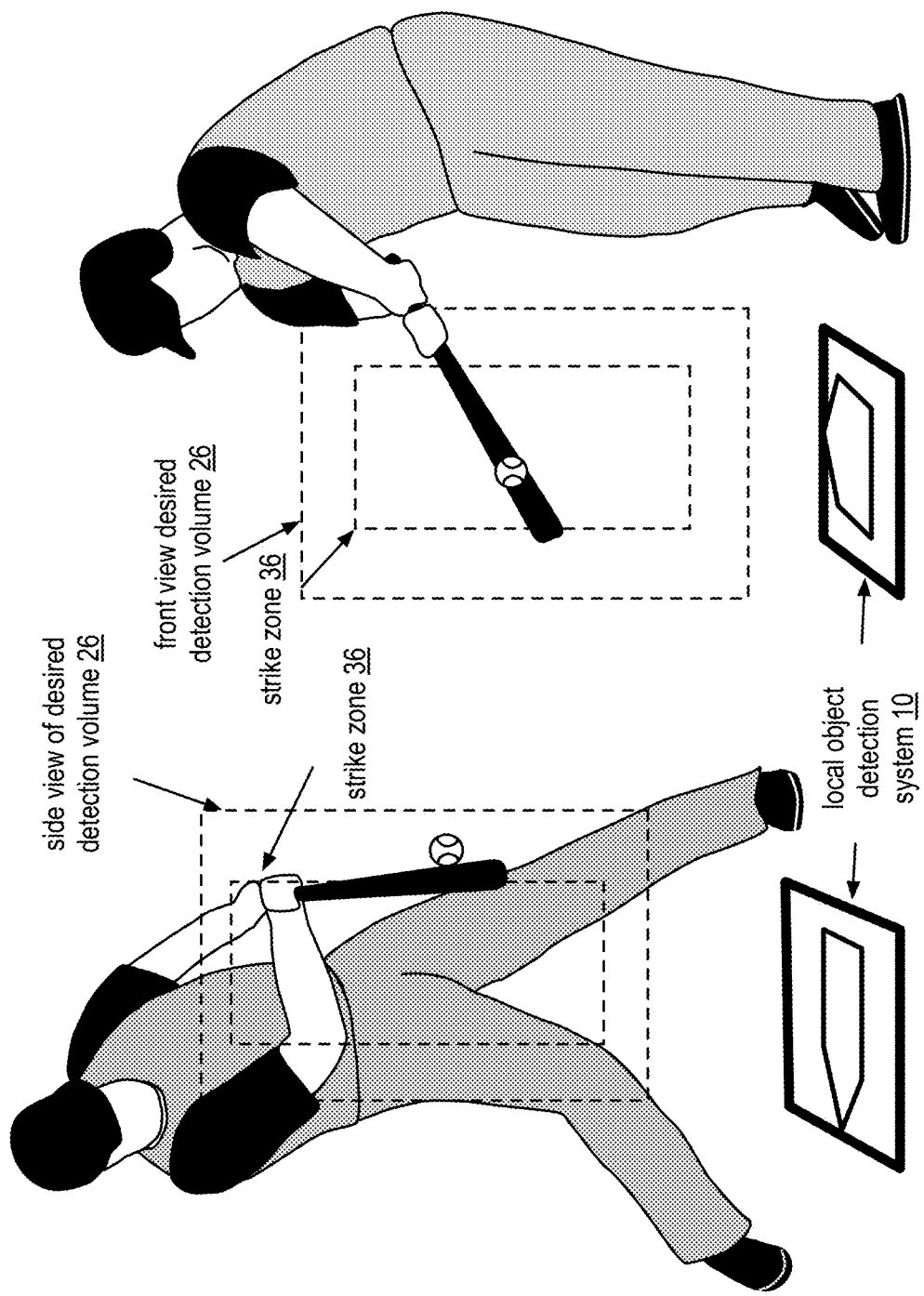

LOCAL OBJECT DETECTION SYSTEM

CROSS REFERENCE TO RELATED PATENTS

The present U.S. Utility Patent Application claims priority pursuant to 35 U.S.C. § 119(e) to U.S. Provisional Application No. 62/376,555, entitled "In-Shoe Ground Reactive Force Measuring System," filed Aug. 18, 2016, which is hereby incorporated herein by reference in its entirety and made part of the present U.S. Utility Patent Application for all purposes.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Technical Field of the Invention

This invention relates generally to radar and more particularly to local object detection using radar techniques.

Description of Related Art

As is known, radar can be used to detect objects. For example, radar systems use radio frequency signals or microwave signals to determine the range, velocity, and/or angle of objects. For example, radar systems use electromagnetic waves to measure distances via one or more techniques that include time-of-flight, frequency modulation, and phased array method. Such radar systems are used in a wide variety of applications.

For example, airport security checkpoints and other security screening locations have implemented full body scanning radar systems to wirelessly detect concealed metallic objects under a person's clothing. Whole body scanning is implemented through the use of backscatter X-ray, active millimeter wave, or passive millimeter wave technology. Backscatter X-ray scanners use weak X-rays to detect radiation that reflects from an object to form an image. Images are taken from both sides of the body to create a two-dimensional (2-D) image of the person and anything else on that person's body.

As is also known, radio frequency identification (RFID) systems include RFID readers and paired RFID tags to track and identify objects through the use of radio frequency (RF) waves. For example, RFID tags are placed on packaging of goods to track their location. In addition, the RFID tag may store information regarding the good such as a serial number, retail price, etc.

As is further known, ultrasound waves are sound waves above 20 kHz and can be used to detect objects and measure distances. For example, ultrasound imaging is often in medical scanning and to test products and structures for invisible flaws.

BRIEF DESCRIPTION OF THE SEVERAL VIEWS OF THE DRAWING(S)

FIG. 1C is a schematic block diagram of an embodiment of an RFID tag in accordance with the present invention;

FIG. 5 is side view of an example of a local object detection system in accordance with the present invention;

FIG. 6 is a front view of an example of a local object detection system in accordance with the present invention;

DETAILED DESCRIPTION OF THE INVENTION

Figure 1A:
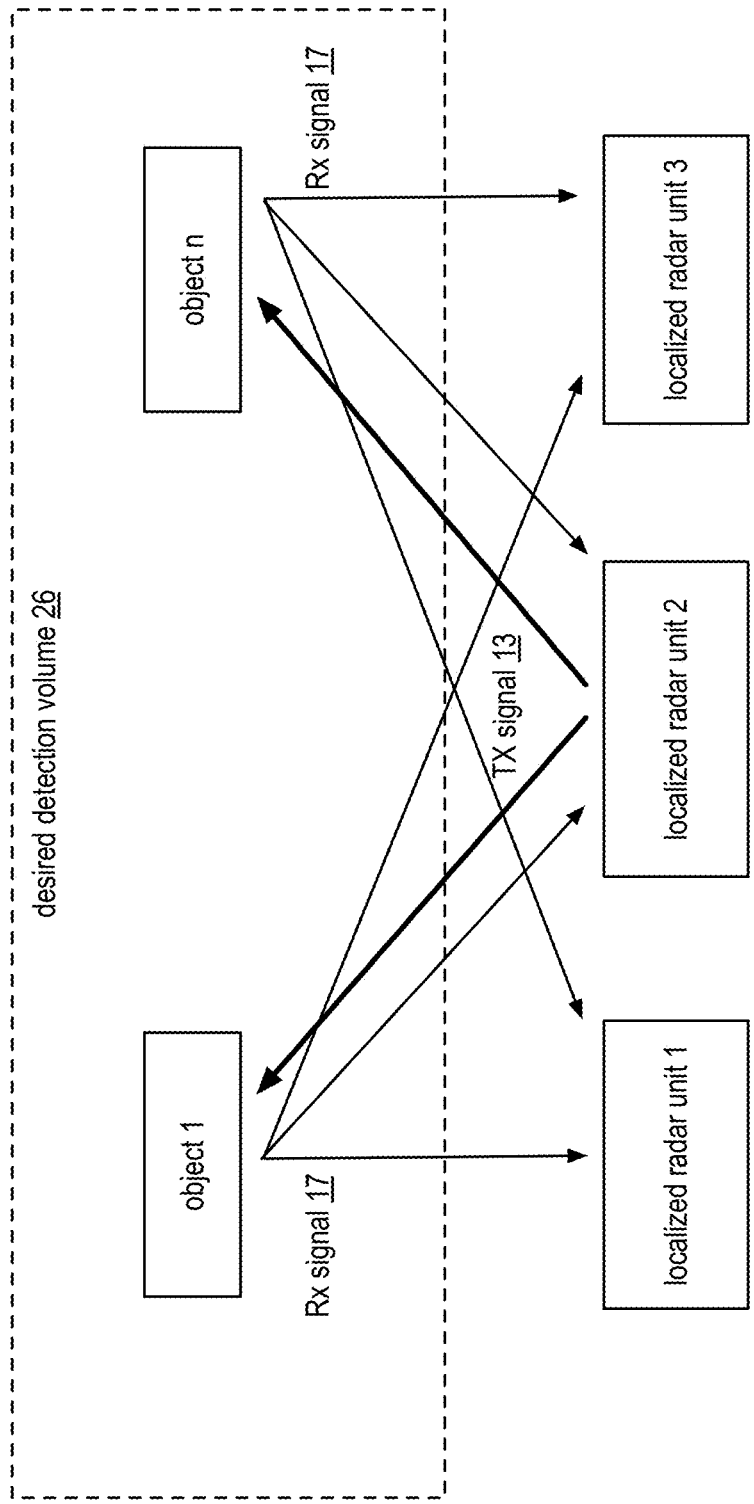
FIG. 1A is a schematic block diagram of an embodiment of local object detection system in accordance with the present invention.

FIG. 1A is a schematic block diagram of a local object detection system 10. The local object detection system 10 includes a plurality of localized radar units (e.g., three shown and labeled as 1-3, but could include more or less localized radar units) to track one or more objects within a desired detection volume 26. The objects 1-n are any tangible object (e.g., a baseball, a package, a tennis racket, etc.) or a point on a body (e.g., a designated marker on a wrist of a human body, a designated marker on a foot of an animal etc.).

One or more of the localized radar units 1-3 transmits outbound transmit signals 13 and one or more of the localized radar units 1-3 receive reflected, refracted, and/or responds signals 17 from an object in order to locate, track, and/or analyze its the movements within the desired detection volume 15. The outbound transmit signals 13 includes radio frequency (RF) signals, ultrasound signals, and/or infrared (IR) signals.

Localized radar units 1-3 each include one or more transmitter sections, one or more receiver sections, and one or more processing modules as will be described in greater detail with reference to one of more subsequent Figures. In general, the transmitter section(s) transmits local radar signals (e.g., RF signals, IR, and/or ultrasound, etc.) within the desired detection volume 26. For an object within the desired detection volume 26 or outside of the volume 26 but in range of the system 10, the transmit (TX) signal(s) 13 will reflect, refract, and/or be absorbed by the object. The reflected and/or refracted signals form the receive (RX) signals 17 that are received by the receiver section. The processing module processes and/or analyzes the received signals 17 to determine whether the object is within the desired detection volume 26. If the object is within the volume 26, the processing module then determines whether the object is one that the system 10 should track. If the object is one that should be tracked, the processing module determines its relative position within the desired detection volume 26 and tracks its movement through the desired detection volume 26.

The desired detection volume 26 may be of a variety of shapes depending on the objects being monitored. For example, the volume 26 could be a cube, a cuboid, a square based pyramid, a cone, a triangular prism, a triangular based pyramid, a cylinder, sphere, or a spheroid. As another example, the volume 26 is a combination of shapes. As a specific example, a cube lower section with an upper section of a cone, square based pyramid, or a triangular prism. As another specific example, the volume 26 includes a cylinder lower section with an upper section of a cone, a half of a sphere, or a half of a spheroid. In yet another example, the volume 26 is an abstract shape that mimics, or encompasses, an outline of a human and the various positions the human body can achieve.

Figure 1B:
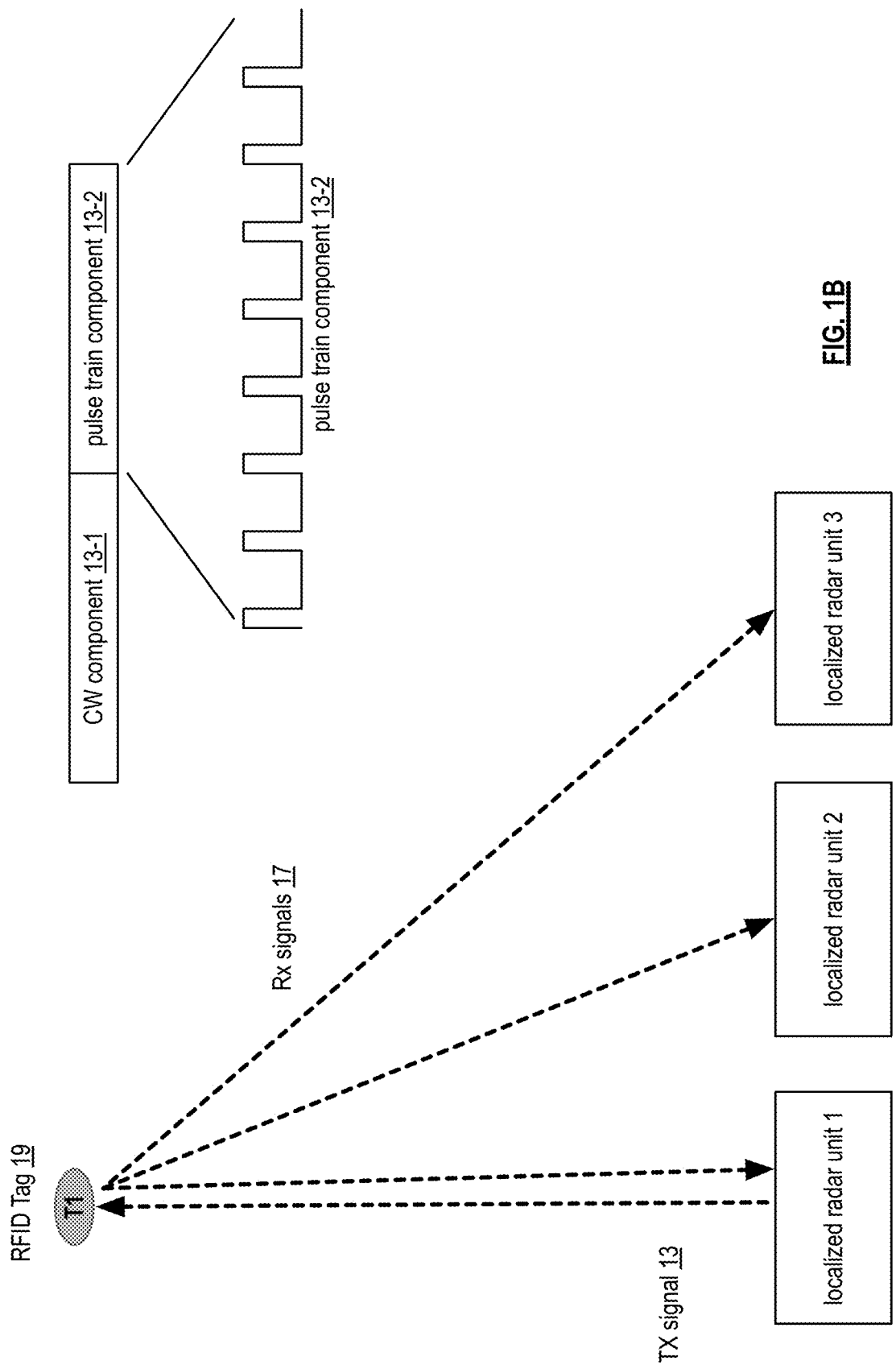
FIG. 1B is a schematic block diagram of an example of local object detection system in accordance with the present invention.

As an example of an RF based radar system and with reference to FIG. 1B, the objects are passive radio frequency identification (RFID) tags 19. For example, RFID tags are placed at different points on a human body (e.g., elbow, wrist, knees, etc.) to track physical movements and position of the body within the desired detection volume 26. As another example, an RFID tag is placed on or in an object (e.g., a baseball, baseball bat, etc.) to track its velocity and movement pattern. The passive RFID tags may use omnidirectional antennas for energy efficiency. In an embodiment, one or more of the localized radar units 1-3 includes an RFID reader to communicate with the passive RFID tags.

For example, a local radar unit transmits an transmit RF signal 13, which includes a continuous wave component 13-1 and a pulse train component 13-2, within the desired detection volume 26. An RFID tag 19 within the proximity of the volume 26 (e.g., in the volume 26 or within a few meters or more) receives the RF signal 13.

FIG. 1C is a schematic block diagram of an embodiment of an RFID tag 19 that includes an antenna 21, a transmission line 23, a power harvesting circuit 25, a clock circuit 27, digital circuitry 29, a low noise amplifier (LNA) 31, a down converter 33, an up converter 35, and a power amplifier (PA) 37. The transmission line 23 couples the antenna 21 to the power harvesting circuit 24, the LNA 31 and the PA 37. Depending on the location of the antenna 21, the transmission line 23 may be a few millimeters long to tens of centimeters long. For example, the circuitry of the RFID tag 19 is on an integrated circuit (IC) and the IC is stitched or otherwise attached to a particular location on a piece of clothing (e.g., elbow of a compression shirt). The antenna 21 is comprises on a metallic thread woven into the clothing in the desired shape of the antenna. The transmission line 23, which may also be metallic thread, couples the metallic thread antenna to the RFID tag circuitry.

In an example of operation, the antenna 21 receives the continuous wave section 13-1 of RF signal 13 from a localized radar unit. The power harvesting circuit 25 converts the continuous wave signal into a supply voltage Vs, which powers the rest of the circuit. Once power is available and the pulse train component 13-2 is being transmitted, the LNA 31 receives it and amplifies it. The down converter 33 converts the received and amplified pulse train into a baseband signal. The digital circuitry 29, which may be implemented as a processing module, processing the baseband pulse train signal (e.g., adjusts amplitude of the pulses, removes noise, adjust rising and falling edge rates, etc.).

The digital circuitry 29 provides the processed pulse train signal to the up converter 35, which converts the processed pulse train signal into an RF signal that is amplified by the PA 37 and transmitted by the antenna 37. The digital circuitry 29, the up converter 35, and/or the PA 37 may use backscattering, Amplitude Shift Keying (ASK), Amplitude Modulation (AM), Frequency Shift Keying (FSK), and/or Phase Shift Keying (PSK) to convert the processed pulse train signal into a transmitted RF signal.

Figure 1D:
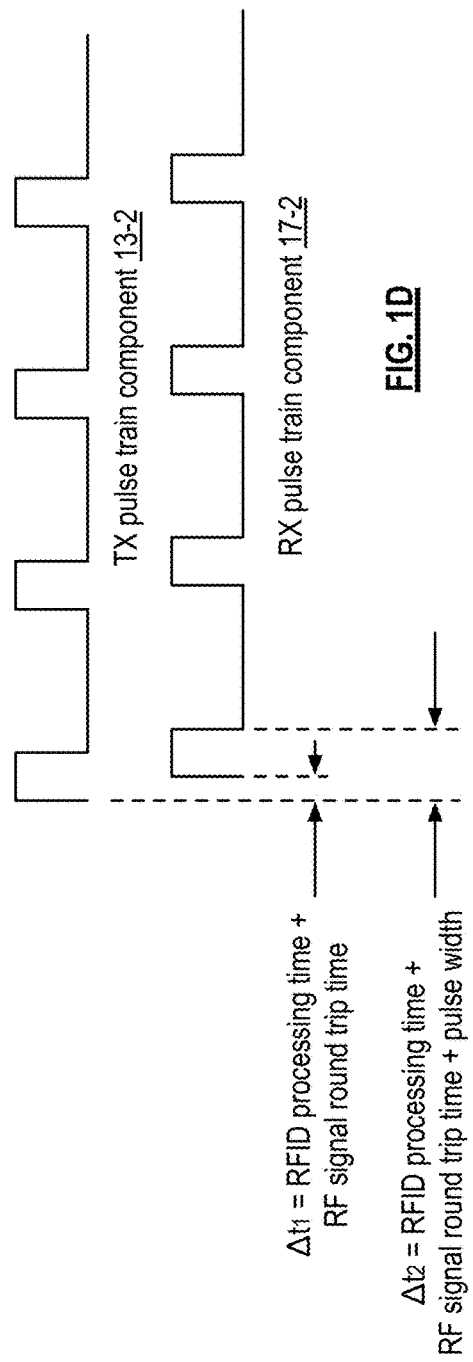
FIG. 1D is a diagram of an example of transmit and receive pulse trains in accordance with the present invention.

FIG. 1D illustrates an example of the transmit pulse train 13-2 and the receive pulse train 17-2, which is produced by the RFID tag as discussed with reference to FIG. 1C and is received by the localized radar units. The TX pulse train 13-2 includes a series of pulses that have a particular pulse width and having a particular pulse rate. For example, the pulse rate is 10 MHz (i.e., 10,000,000 pulses per second), where the period is (1/10,000,000 or 100 nano seconds (nSec), and a pulse width of 25 nSec. In other examples, the pulse rate ranges from 1 KHz to 100 MHz or more.

With the RFID tag 19 echoing back the pulse train, there is some time for it to process the pulse train and time for it to be transmitted to the localized radar units as the RX pulse train component 17-2. Accordingly, there is a time delay (e.g., $\Delta t_1$, which equals the RFID tag processing time plus round trip time for the RF signal) between the leading edge of a TX pulse and a corresponding leading edge of an RX pulse. The time delay may also include the pulse width (e.g., $\Delta t_2$, which equals the RFID tag processing time plus round trip time for the RF signal).

As is known, the RF signal travels at the speed of light (e.g., $3\times10^8$ meters/sec or 30 centimeters/nSec, 186,000 miles/sec or 0.982 ft/nSec). As such, the round trip time for the RF signal to reach the RFID tag from the localized radar unit and for it return can be used to determine the distance between the localized radar unit and the tag. Three or more distances between the tag and localized radar units can be used in a location-triangulation function to determine the position of the object.

Determining the round trip time has two primary issues: the first being that the distance between the object and local radar units is relatively small such that the travel time of the RF signals is very short and the second issue being that the round trip time includes the processing time of the RFID tag. One solution to address the processing time of the tag is place the tag in a predetermined position that is at known distance from each of the localized radar units and measure the round trip times of the RF signals. With the known distance, the RF signal transmit time between the radar units and the tag is readily calculated. The calculated RF signal time is then subtracted from the measure round trip time to determine the processing time of the RFID tag to echo the pulse train. For example, if the tag is place 0.982 feet from a radar unit, the time for the signal to travel from the radar unit to the tag is 1 nSec. As such, the round trip time of the RF signal only is 2 nSec. If the measured round trip time is 32 nSec, then the processing time of the tag is calculated to be 30 nSec. The tag and/or the localized radar units can store the calibration information so it does not need to be performed each use of the system.

Figure 1E:
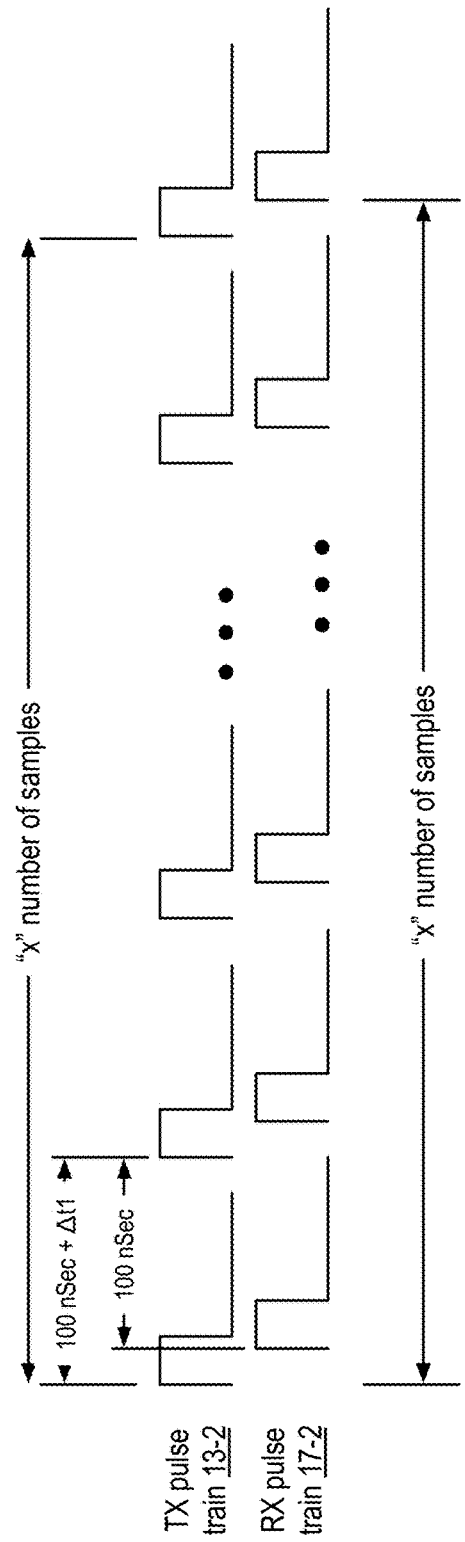
FIG. 1E is a diagram of another example of transmit and receive pulse trains in accordance with the present invention.

To address the short distance and very short RF signal travel time, a solution includes looking at multiple pulses to determine the travel time. For example, and as shown in FIG. 1E, a first TX pulse is sent at some time later (e.g., $\Delta t_1$) a corresponding pulse of the RX pulse train 17-2 is received. At leading edge of this RX pulse, the next interval for a pulse of the TX pulse train is triggered such that the pulse time period is 100 nSec+$\Delta t_1$. If $\Delta t_1$ is 32 nSec, then the new pulse time interval is 132 nSec, which is an effective rate of 7,575 Mhz.

If ten pulses are grouped, then the time for the ten pulses is measured to be 1.32 μSec. The 1.32 μSec is divided by 10 to get 132 nSec. With a known clock offset of 100 nSec, the round trip time is calculated to be 32 nSec. With the known processing time of 30 nSec, then the RF signal time is 2 nSec. From the 2 nSec, the distance between the tag and the local radar unit is determined. Note the processing time of the localized radar unit may also need to be calculated and factored out to establish the true RF signal travel time between the radar unit and the tag.

As an example of an RF based radar system, the tags are replaced with RF reflectors off of which RF signals bounce. In this example, there is no processing time for the tag. Thus, the measure time is for the round trip of the RF signal only.

As another example of an RF based radar system, the object is a ball, a bat, etc., of which the RF signals bounce. Again, there is no processing time for the tag. Thus, the measure time is for the round trip of the RF signal only.

Figure 2:
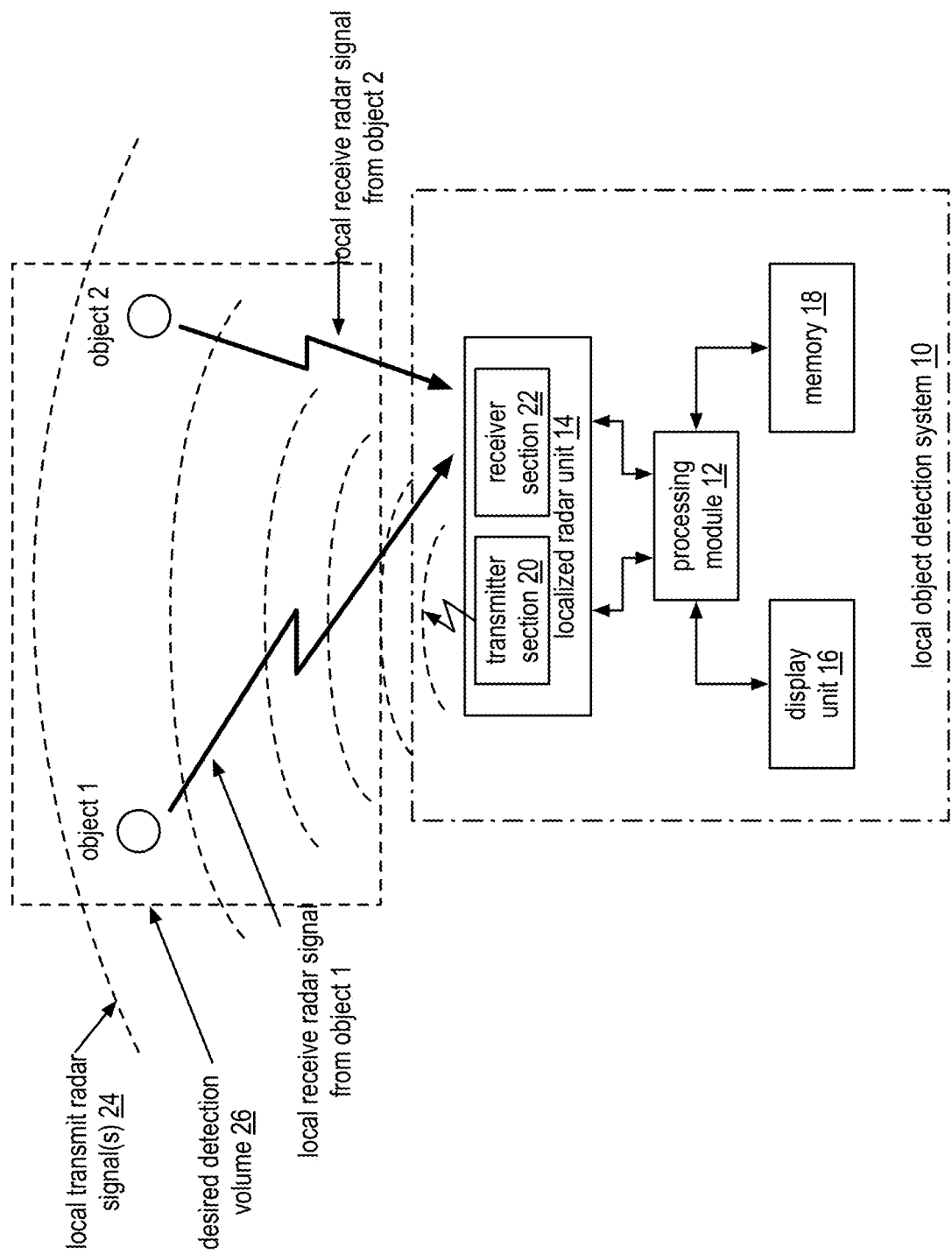
FIG. 2 is another schematic block diagram of another embodiment of a local object detection system in accordance with the present invention.

FIG. 2 is another schematic block diagram of a local object detection system 10 that includes a processing module 12, a localized radar unit 14, a display unit 16, and memory 18. The localized radar unit 14 includes a transmitter section 20 that includes one or more transmitters and a receiver section 22 that includes one or more receivers. The local object detection system 10 operates to detect and track objects within a desired detection volume 26. The localized radar unit 14, processing module 12, display unit 16, and memory 18 may be separate devices or integrated as common devices. The desired detection volume 26 is a three-dimensional space defined by a Cartesian coordinate system or a Polar coordinate system with respect to a reference point, where the reference point (e.g., origin of coordinate system) is based on location of the transmitter section.

For example, when the local object detection system's application is tracking human body movement, the desired detection volume 26 may be a volume of space surrounding the human body in which body movements would be plausible. As an example, if a transmitter section is located in a person's shoe, then the shoe would be the reference point and the desired detection volume 26 is a reasonable volume with respect to the shoe (e.g., a leg length in the x and y directions and a height plus possible jump length in the z direction) to account for a body's movement. Any objects detected outside this desired detection volume would be disregarded. As another example, if the desired application of the local object detection system 10 is to track a baseball while it nears and/or enters a strike zone, the desired detection volume 26 is the strike zone area in reference to a transmitter section located in a home plate.

In an example of operation, the transmitter section 20 of the localized radar unit 14 transmits one or more local transmit radar signals 24. The local transmit radar signal(s) 24 include one of a radio frequency (RF) signal, an infrared signal, and an ultrasound signal. The receivers of the receiver section 22 of the localized radar unit 14 receive local receive radar signals that corresponds to the local transmit radar signals begin reflected or refracted off an object (e.g., RF signals reflected or refracted off a passive RFID tag on a body, baseball, etc.). For example, local transmit radar signals(s) 24 are reflected or refracted off object 1 and the receiver section 22 receives the reflected or refracted signal off object 1 as a local receive radar signal for object 1.

As another example, local transmit radar signals(s) 24 are reflected or refracted off object 2 and the receiver section 22 receives the reflected or refracted signal off object 2 as a local receive radar signal from object 2. The processing module 12 processes the local receive radar signal from object 1 and the local receive radar signal from object 2 to determine a relative distance of object 1 and object 2. The distance between each object and the various localized radar units are used to determine a relative position of the objects in the volume 26. For example, the processing unit 12 utilizes a triangulation location function of three or more of the distances calculated from the local receive radar signals with respect to a reference point to determine the relative position of object 1 and object 2.

When the relative position of object 1 and object 2 is determined, the processing module 12 determines whether object 1 and object 2 are positioned within the desired detection volume 26. For example, the processing module 12 interprets the relative positions of object 1 and object 2 as coordinates (e.g., of a Cartesian coordinate system or a Polar coordinate system) relative to a reference point and compares those coordinates to the three-dimensional space defined by a Cartesian coordinate system or a Polar coordinate system of the desired detection volume 26. Alternatively, the processing module 12 recognizes an object that is not within the desired detection volume 26 but is within a certain distance of the desired detection volume 26 and is on a trajectory leading into the desired detection volume 26. Here, the processing module 12 has determined that object 1 and object 2 are in the desired detection volume 26, and the processing module 12 further processes the local receive signals reflecting off of object 1 and object 2 to determine a movement pattern of object 1 and object 2 (e.g., a baseball entering a strike zone, an RFID tag located on a person's moving arm).

The processing module 12 determines whether the movement pattern is within a range of plausible movements for the object. For example, if local object detection system 10 is detecting a baseball entering a strike zone, plausible movements for the object would include trajectories representative of common pitching movements (e.g., a curve ball, fastball, etc.). If for instance, object 1 is plunging straight down through the desired detection volume 26 as if the object was dropped by the batter and not thrown as a pitch, this movement would be considered implausible for the desired tracking application. An object with implausible movement is likely not the object that the system intended to track and will be disregarded.

Similarly, the processing module 12 processes the local receive radar signals to determine a relative velocity as part of the movement pattern. Determining whether the movement pattern of the object is within a range of plausible movements for the object includes determining that the relative velocity is within an anticipated velocity range of the object. For example, if the local object detection system 10 is detecting a baseball entering a strike zone, the anticipated velocity range for the object would include all possible pitching velocity (e.g., 75 mph or greater for college and professional players). A velocity outside this range of plausible pitching velocities would not be plausible. For instance, a baseball moving far too slow through the desired detection volume 26 may just be hand carried and not intended for tracking. An object with implausible velocity is likely not the object that the system intends to track and will be disregarded. When the movement pattern of the object is within a range of plausible movements and/or velocities for the object, the processing module 12 tracks the movement of the object within the desired detection volume 26.

The movement tracking data produced by the processing module 12 may be stored in memory 18 for analysis and/or displayed on the display unit 16. The movement tracking data may also be sent to another computing device (e.g., a smart phone) for storage and/or display.

Figure 3:
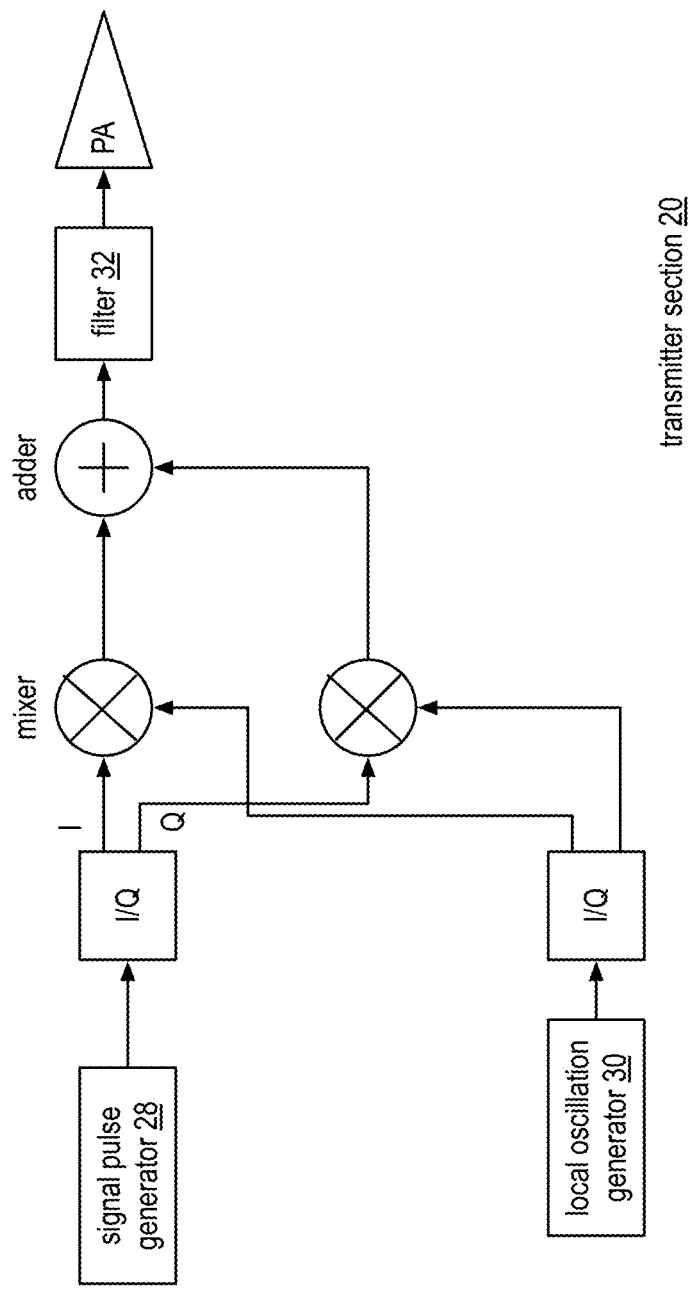
FIG. 3 is a schematic diagram of an embodiment of a transmitter section of the localized radar unit in accordance with the present invention.

FIG. 3 is a schematic diagram of a transmitter section 22 of the localized radar unit. The transmitter section 22 includes one transmitter however the transmitter section 22 may include multiple transmitters. The transmitter section 22 includes a signal pulse generator 28, a local oscillation generator 30, IQ phase shift modules, mixers, an adder, a filter 32, and a power amplifier (PA).

In an example of operation, the signal pulse generator 28 generates a pulse reference signal (e.g., a 30 KHz continuous wave sinusoidal reference signal, and 10 MHz pulse train, etc.). The IQ phase shift module generates an in-phase pulse reference signal (0° phase shift) and a quadrature pulse reference signal (90° phase shift). The local oscillation generator 30 generates a transmitter local oscillation (e.g., 800 MHz to 60). The second IQ phase shift module generates an in-phase local oscillation signal (0° phase shift) and a quadrature local oscillation signal (90° phase shift). A first mixer mixes the in-phase pulse reference signal (e.g., sin $\Phi(t)$) with the in-phase local oscillation (e.g., sin $\omega_{LO}(t)$) to produce a first up-converted signal component (e.g., ½*cos($\omega_{LO}(t) - \Phi(t)$) − ½*cos($\omega_{LO}(t) + \Phi(t)$)).

A second mixer mixes the quadrature reference signal (e.g., cos $\Phi(t)$) with the quadrature local oscillation signal (e.g., cos $\omega_{LO}(t)$) to produce a second up-converted signal component (e.g., ½*cos($\omega_{LO}(t) - \Phi(t)$)+½*cos)$\omega_{LO}(t)+\Phi(t)$)). The adder sums the first up-converted signal component and the second up-converted signal component (e.g., ½*cos($\omega_{LO}(t) - \Phi(t)$)−½*cos($\omega_{LO}(t) + \Phi(t)$)+½*cos($\omega_{LO}(t) - \Phi(t)$)+½*cos($\omega_{LO}(t) + \Phi(t)$)=cos($\omega_{LO}(t) + \Phi(t)$)). The filter 32 (e.g., an RF bandpass filter) filters the signal and the power amplifier amplifies the signal for transmission.

Figure 4:
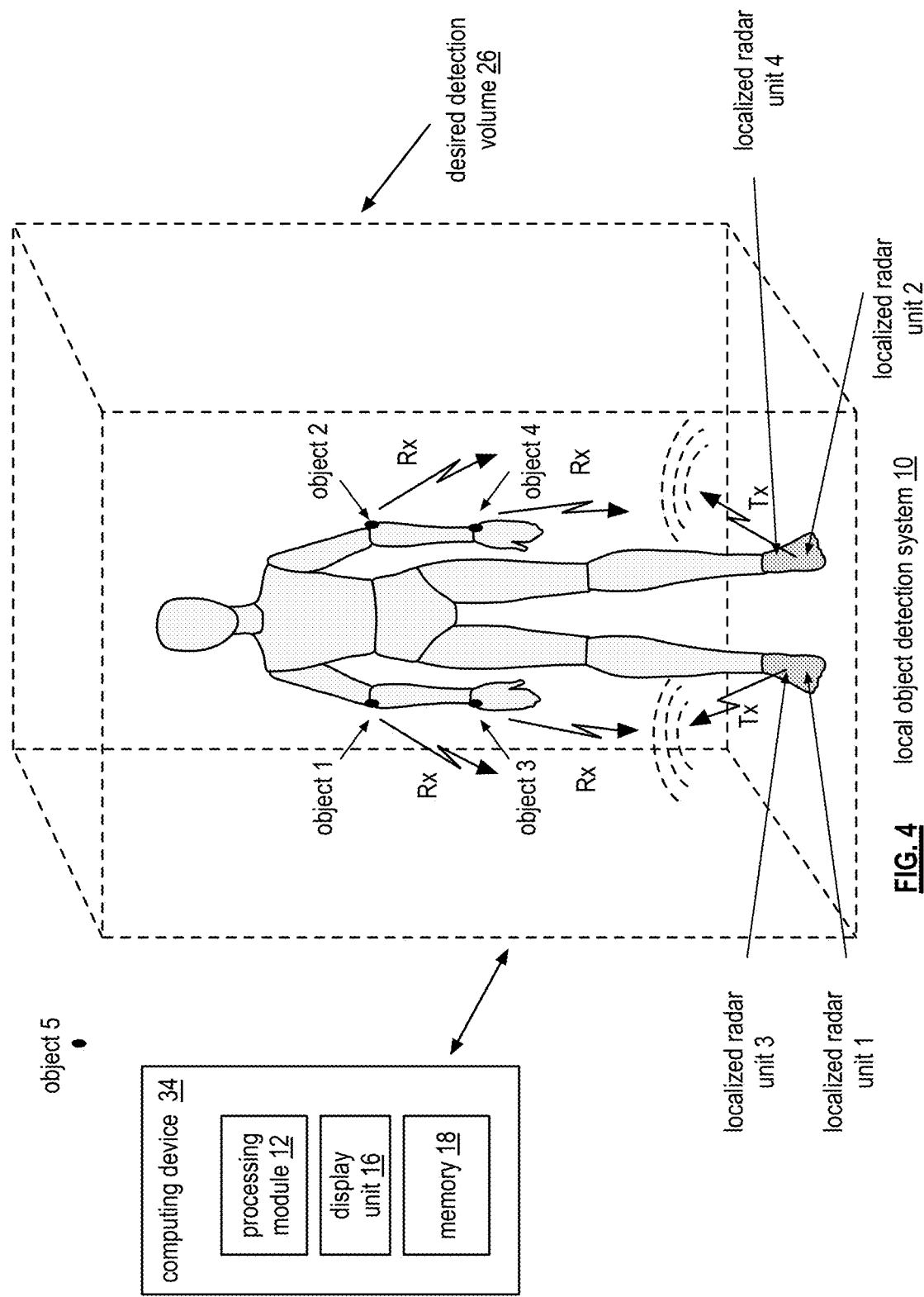
FIG. 4 is a schematic diagram of another embodiment of a local object detection system in accordance with the present invention.

FIG. 4 is an example of a local object detection system 10 that includes localized radar units 1-4 (two in the left shoe and two in the right shoe; one in the forefoot of the shoe and the other in the heel), desired detection volume 26, and computing device 34. Computing device 34 includes processing module 12, display unit 16, and memory 18. Computing device 34 may each be a portable computing device and/or a fixed computing device. A portable computing device may be a social networking device, a cell phone, a smart phone, a smart watch, a digital assistant, a digital video player, a laptop computer, a handheld computer, a tablet, and/or any other portable device. A fixed computing device may be a computer (PC), a computer server, and/or any type of home or office computing equipment. Note that each of the localized radar units 1-2 and the computing device may be separate devices or integrated as common.

Localized radar units 1-4 are located on the right and left shoe respectively (e.g., embedded in the shoe, affixed onto the laces or outsole, etc.) of the monitored person. Objects 1-4 are tags (e.g., passive RFID tags) located on the elbows and wrists of a human body. For simplicity, only four tags are shown but an array of tags (e.g., 20 tags) could be placed on various critical points of the body to measure movement. The desired detection volume 26 includes space around the human body where body movement could plausibly occur. Object 5 is an object (e.g., a passive RFID tag on another person, a ball, a bird, etc.) located outside the desired detection volume. For example, object 5 may be on a nearby person using a different local object detection system (e.g., two participants in an athletic event interested in tracking movements for performance purposes). The localized radar units function as previously discussed to determine distances, determine positions, and/or determine movement of objects 1-4.

In an example, one or more of the localized radar units 1-4 transmit local transmit radar signals (e.g., RF signals, IR signals, ultrasound signals, etc.). The localized radar units 1-4 receive local receive local receive radar signals that correspond to the local transmit radar signals being reflected or refracted off objects 1-4 and possibly object 5 if object 5 is within range. The localized radar units 1-4 communicate the received signals to the processing module 12 of the computing device 34 (e.g., a smart phone or watch). The processing module 12 processes the local receive radar signals to determine a relative position of the objects. For example, the processing module 12 utilizes a triangulation location function of three or more of the local receive radar signals with respect to a reference point to determine the relative position.

The processing module 12 then determines whether the relative positions of the objects detected are within the desired detection volume 26. For example, the processing module 12 interprets the relative positions of the objects as coordinates (e.g., of a Cartesian coordinate system or a Polar coordinate system) relative to a reference point and compares those coordinates to the three-dimensional space defined by a Cartesian coordinate system or a Polar coordinate system of the desired detection volume 26. The processing module 12 is further operable to recognize known objects (e.g., by a resonant frequency and/or ID associated with an RFID tag) to identify specific objects. For example, processing module 12 identifies object 1 as being within the desired detection volume 26 and further identifies object 1 as the right elbow tag based on a known tag lookup.

Because object 5 is outside of the desired detection volume 26, the processing module 12 disregards any local receive radar signals it may receive regarding object 5. The processing module 12 then determines whether the movement pattern of objects 1-4 are within a range of plausible movements for the objects. A range of plausible movement patterns for objects 1-4 may include a variety of patterns that make sense for upper body movement. The processing module 12 may also determine whether the velocity of the objects is within an anticipated range. For example, if object 1 has a very high velocity that would be implausible for human movement, object 1 may be disregarded for tracking purposes.

When objects 1-4 are within the range of plausible movements and/or velocities for the objects, the processing module 12 tracks the movement of the objects within the desired detection volume 26. The computing device 34 can store the tracked movement in memory 18 and/or display the data on the display unit 16. For example, the display unit 16 (e.g., a display screen on the device) may display the tracked movement mapped onto an animated avatar. As another example, the tracked movement may be displayed as graphical and/or analytical data.

FIGS. 5 and 6 are examples of local object detection system 10. FIG. 5 shows the side view of a desired detection volume 26 that includes a strike zone 36. FIG. 6 shows a front view of the desired detection volume 26 that includes the strike zone 36. The local object detection system 10 is shown here as a baseball in/out strike zone system to be used in a hitting area (e.g., embedded in a home base, a mat or device placed over or under a home base, a mat or device placed on the ground of a designated hitting area, etc.). The local object detection system 10 transmits local transmit radar signals (e.g., RF signals, IR signals, ultrasound signals, etc.) and receives local receive radar signals that correspond to the transmit radar signals being reflected or refracted off the baseball and/or off the bat. The processing module of the local object detection system 10 processes the local receive radar signals to determine a relative position of the baseball and/or the bat. For example, the processing module utilizes a triangulation location function of three or more of the local receive radar signals with respect to a reference point to determine the relative position.

The processing module determines whether the bat and/or ball are positioned within the desired detection volume 26. When the bat and/or ball are positioned in the desired detection volume 26, the processing module further determines the movement pattern of the bat and/or ball and whether the movement patterns are plausible. The processing module may also determine a velocity of the bat and/or ball and whether the velocity is within an anticipated range of velocities of the bat and/or ball. If the movement pattern and/or velocity of the bat and/or ball are not plausible, tracking the object is disregarded since it is probably not a baseball or a bat.

Based on the movement pattern, velocity, and other identifiers (e.g., resonant frequency of the object's RFID tag, the identification of the RFID tag, etc.) of the objects the processing module identifies the objects (e.g., one object is bat and one is a baseball) and tracks the movement of the object in the desired detection volume 26. The object identified as the baseball is tracked as it moves through the desired detection volume 26 and into or out of the strike zone 36. The processing module is operable to map the movement of the baseball through the strike zone 36 and display this path directly onto a display unit (e.g., an LED light path on the mat placed over the home base).

Because the movement of the baseball bat is also tracked, the point of contact between the baseball and bat can be identified and displayed on the local object detection system's display unit. The processing module determines a contact point of the bat colliding with the baseball based on the movements and positions of the baseball and the bat within the desired detection volume. Various types of display units for this application are discussed in greater detail with reference to FIGS. 10-17.

Figures 7, 8:
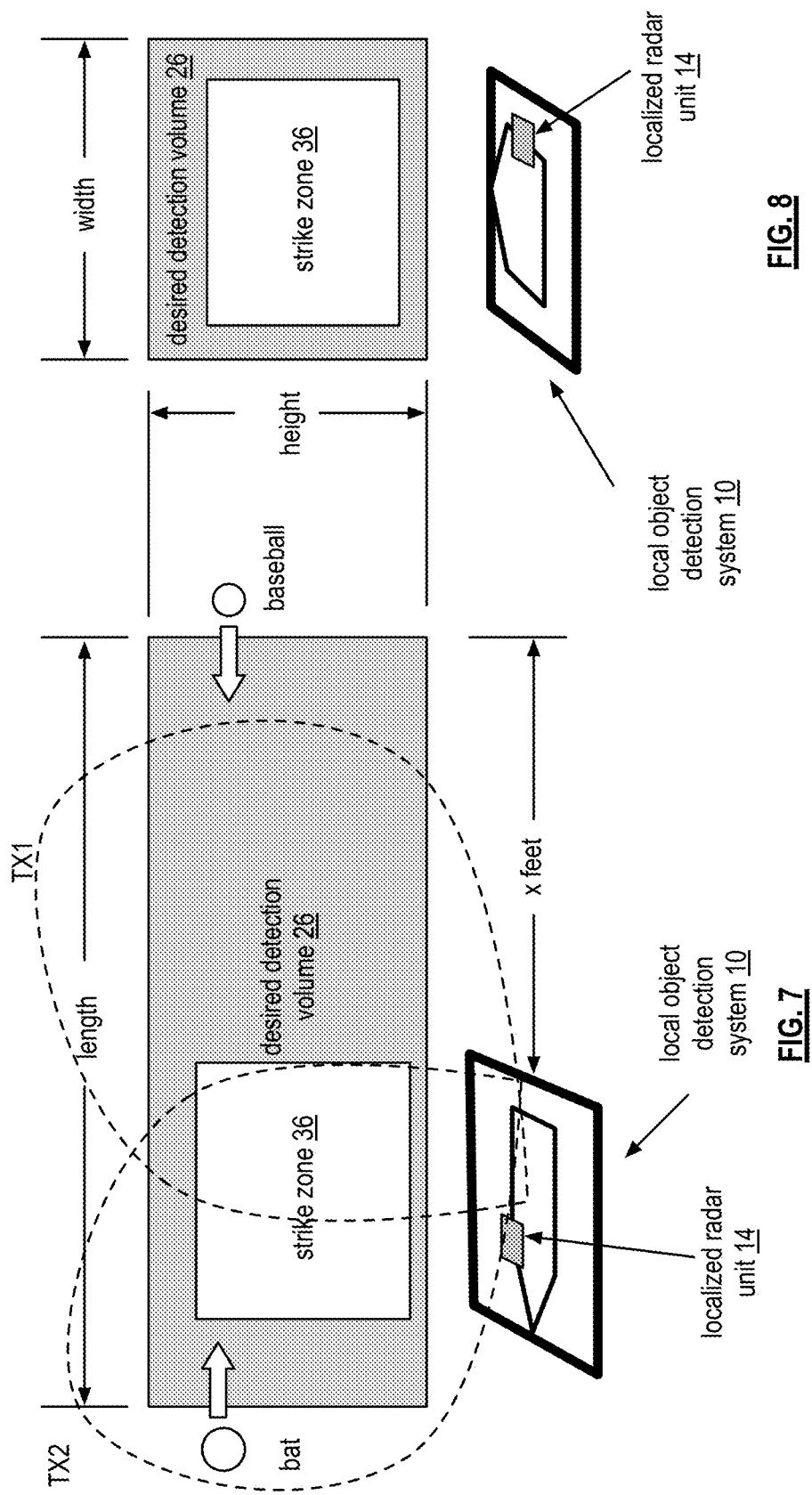
FIG. 7 is a side view schematic block diagram of an embodiment of a local object detection system in accordance with the present invention.
FIG. 8 is a front view schematic block diagrams of an embodiment of a local object detection system in accordance with the present invention.

FIGS. 7 and 8 are schematic block diagrams of a local object detection system 10. FIG. 7 shows the side view of the local object detection system 10 and FIG. 8 shows the front view of the local object detection system 10 with respect to a home base/baseball hitting zone. The local object detection system 10 shown in FIGS. 7 and 8 is implemented as a mat (e.g., to be placed over a home base or in a hitting area) that includes the localized radar unit 14 and may also include the processing module 12, display unit 16, and memory 18. The processing module 12, display unit 16, and memory 18 may alternatively be located on a separate device.

The desired detection volume 26 of FIGS. 7 and 8 includes strike zone 36. The desired detection volume 26 is a three-dimensional space defined by a Cartesian coordinate system or a Polar coordinate system with respect to a reference point, where the reference point (e.g., origin of coordinate system) is based on location of the transmitter section. Here, the transmitter section is located within the localized radar unit 14 which is in the mat over the home base. In addition to encompassing the strike zone 36, the desired detection volume 26 includes an amount (e.g., x feet) in front of the home base in order to detect an incoming baseball, a space behind the home base to detect a baseball bat, and an area (a reasonable height and length) surrounding the strike zone 36 to detect when a ball is outside the strike zone 36.

The localized radar unit 14 transmits local transmit radar signals (e.g., RF signals, IR signals, ultrasound signals, etc.) shown in FIGS. 7 as TX1 and TX2. TX1 and TX2 are transmitted such that the signals collectively cover the desired detection volume 26. The localized radar unit 14 receives local receive radar signals that correspond to the transmit radar signals being reflected or refracted off an object (e.g., the bat and the baseball). The processing module of the local object detection system 10 processes the local receive radar signals to determine a relative position of the object. For example, the processing module utilizes a triangulation location function of three or more of the plurality of local receive radar signals with respect to a reference point to determine the relative position.

The processing module determines whether the objects are positioned within the desired detection volume 26. When the objects are positioned in the desired detection volume 26, the processing module further determines the movement pattern of the objects and whether the movement patterns are plausible. The processing module may also determine a velocity of the object and whether the velocity is within an anticipated range of velocities of the object. If the movement pattern and/or velocity of the object are not plausible, tracking the object is disregarded. Based on the movement pattern, velocity, and other identifiers (e.g., resonant frequency of the object's RFID tag, the identification of the RFID tag, etc.) of the objects the processing module identifies the objects (e.g., one object is bat and one is a baseball) and tracks the movement of the object in the desired detection volume 26. The object identified as the baseball is tracked as it moves through the desired detection volume 26 and into or out of the strike zone 36. The processing module is operable to map the movement of the baseball through the strike zone 36 and display this path directly onto a display unit (e.g., an LED light path on the mat).

Because the movement of the baseball bat is also tracked, the point of contact between the baseball and bat can be identified and displayed on the local object detection system's display unit. Various types of display units for this application are discussed in greater detail with reference to FIGS. 10-17.

Figure 9:
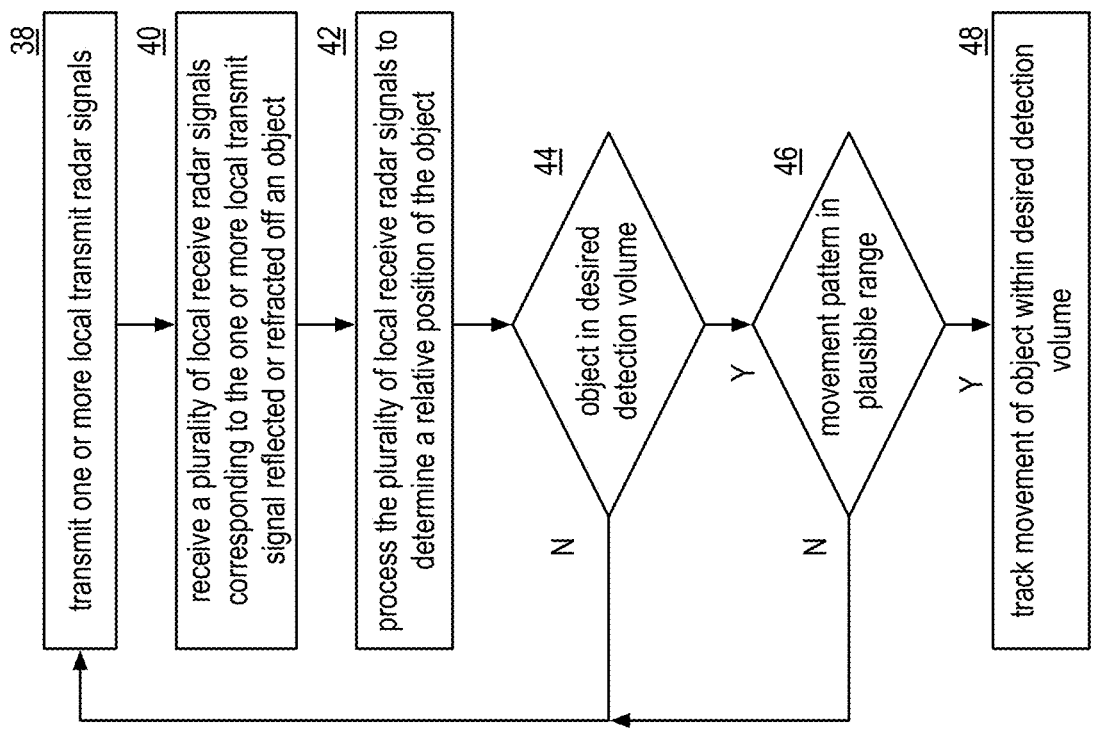
FIG. 9 is a logic diagram of an example of a method of a local object detection in accordance with the present invention.

FIG. 9 is a logic diagram of an example of a method of a local object detection. The method begins with step 38 where a transmitter section of a local object detection system transmits one or more local transmit radar signals. A local transmit radar signal of the one or more local transmit radar signals include one of a radio frequency (RF) signal, an infrared signal, and an ultrasound signal. The method continues with step 40 where a plurality of receivers of the local object detection system receive a plurality of local receive radar signals that corresponds to the one or more local transmit radar signals being reflected or refracted off an object. For example, the object may be a passive RFID tag located on a person, animal, package, or any other physical item.

The method continues with step 42 where the processing module of the local object detection system processes the plurality of local receive radar signals to determine a relative position of the object. For example, the processing module utilizes a triangulation location function of three or more of the plurality of local receive radar signals with respect to a reference point to determine the relative position.

The method continues with step 44 where the processing module determines whether the object is positioned within a desired detection volume associated with a position of the transmitter section. The desired detection volume is a three-dimensional space defined by a Cartesian coordinate system or a Polar coordinate system with respect to a reference point, where the reference point (e.g., origin of coordinate system) is based on location of the transmitter section. If the object is located within the desired detection volume, the method continues with step 46. If not, the method branches back to step 38 where the transmitter section transmits one or more local transmit radar signals.

Alternatively, the processing module may also recognize an object that is not within the desired detection volume but is within a certain distance of the desired detection volume or on a trajectory leading into the desired detection volume. If those points are of interest, the method will continue to step 46 where the processing module determines whether the movement pattern of the object is within a range of plausible movements for the object. For example, if local object detection system is detecting a baseball entering a strike zone, plausible movements for the object would include trajectories representative of common pitching movements (e.g., a curve ball). An object with implausible movement is likely not the object that the system intended to track and will be disregarded.

The processing module may further process the plurality of local receive radar signals to determine a relative velocity as part of the movement pattern. Determining whether the movement pattern of the object is within a range of plausible movements for the object includes determining that the relative velocity is within an anticipated velocity range of the object. When the movement pattern of the object is not within a range of plausible movements and/or velocities for the object, the method branches back to step 38 where the transmitter section transmits one or more local transmit radar signals.

When the movement pattern of the object is within a range of plausible movements and/or velocities for the object, the method continues to step 48 where the processing module tracks movement of the object within the desired detection volume. The movement tracking data produced by the processing module may be stored for analysis and/or displayed. The movement tracking data may also be sent to another computing device (e.g., a smart phone) for storage and/or display.

Figure 10:
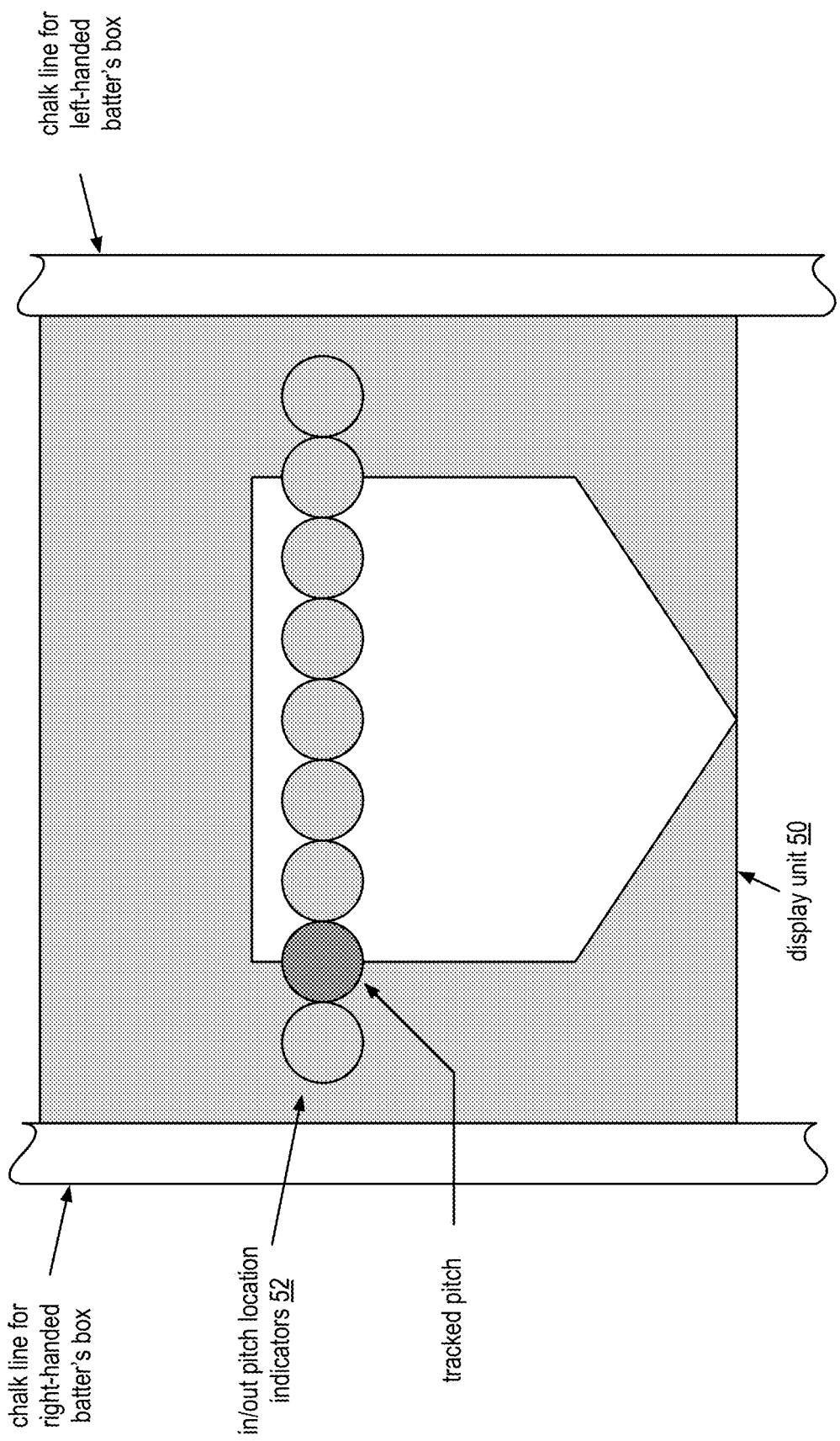
FIG. 10 is a diagram of an embodiment of a display unit of a local object detection system in accordance with the present invention.

FIG. 10 is an example of a display unit 50 of a local object detection system. The local object detection system shown is a mat for use in detecting whether baseballs are in or out of a strike zone (refer to FIGS. 6-8 for a more detailed discussion). The display unit 50 includes in/out pitch location indicators 52 that run the length of the mat. An indicator is illuminated (e.g., via LED) on the display unit 50 to identify the path of the baseball in relation to the strike zone. When a baseball is detected, located, and mapped by the processing module of the local object detection system, the processing module determines to illuminate one indicator that best represents the baseball's tracked path. For example, a baseball tracked going down the center of the mat/plate will illuminate the center indicator (shown here as circular shapes to represent baseballs). As another example, a baseball that is out of the strike zone and to the left will illuminate the far left indicator.

Figure 11:
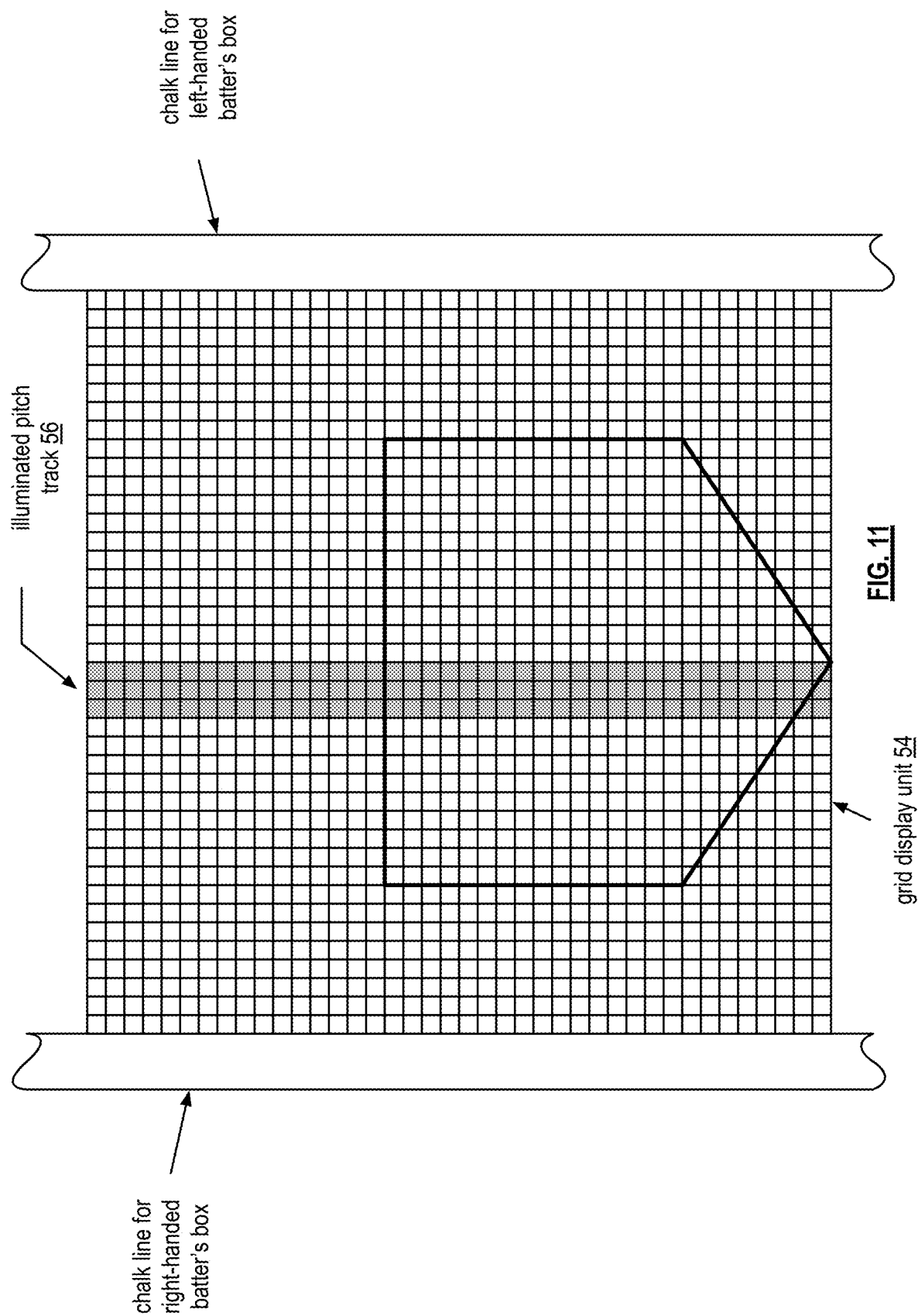
FIG. 11 is a diagram example of another embodiment of a display unit of a local object detection system in accordance with the present invention.

FIG. 11 is another example of a display unit 54 of a local object detection system. The local object detection system shown is a mat for use in detecting whether baseballs are in or out of a strike zone (refer to FIGS. 6-8 for a more detailed discussion). The mat shown features a grid display unit 54 that covers the entire mat. Each block of the grid is capable of illuminating such that a full path of a baseball can be mapped onto the grid display unit 54. A pitch track 56 is illuminated (e.g., via LED) on the display unit 54 to identify the path of the baseball in relation to the strike zone. When a baseball is detected, located, and mapped by the processing module of the local object detection system, the processing module communicates that path as an illuminated path approximately the width of the baseball. For example, a baseball tracked going slightly to the left of the center of the mat/plate will illuminate a path similar to what is shown.

Figure 12:
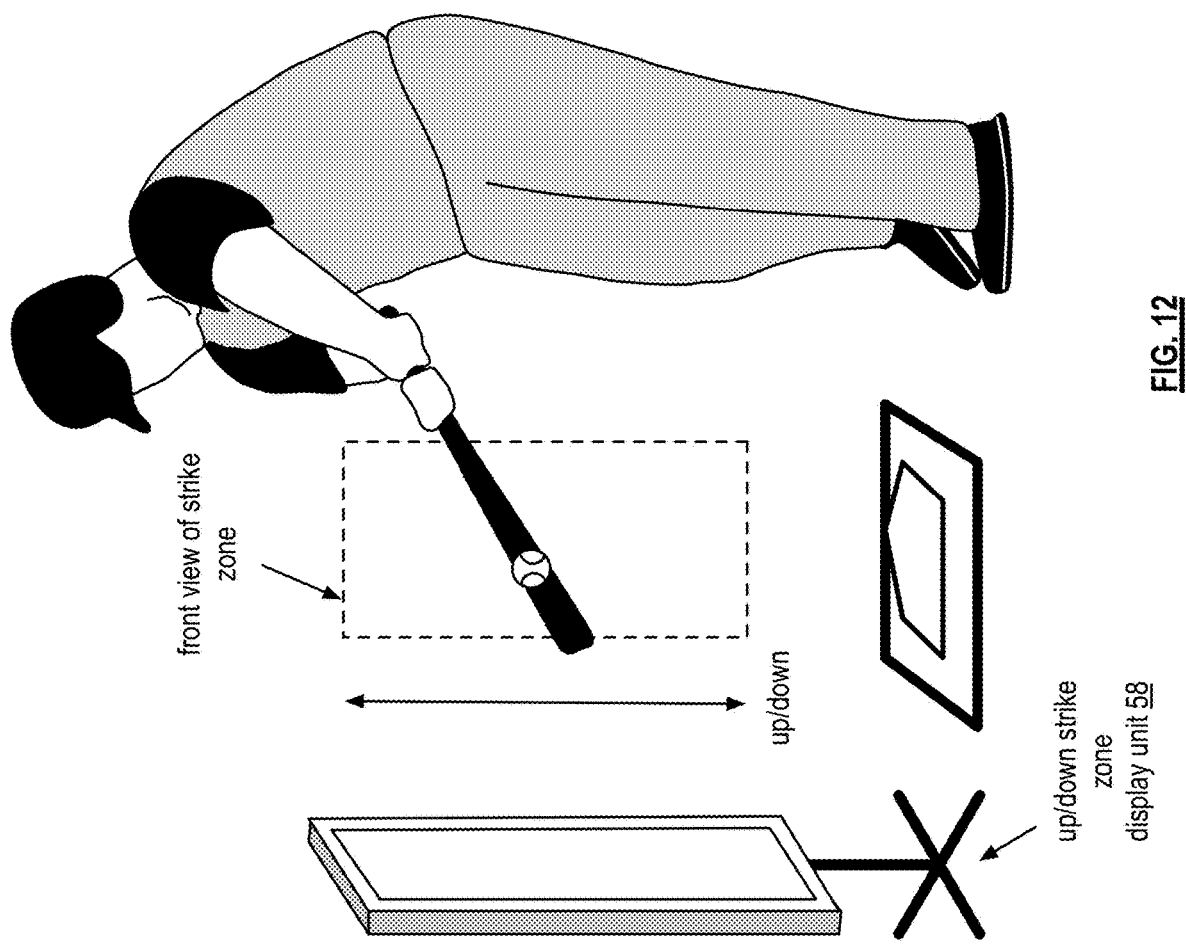
FIG. 12 is a diagram of another embodiment of a display unit of a local object detection system in accordance with the present invention.

FIG. 12 is another example of a display unit 58 of a local object detection system. The local object detection system shown is a mat for use in detecting whether baseballs are in or out of a strike zone (refer to FIGS. 6-8 for a more detailed discussion). In this example, the display unit is not integrated into the mat or the home base but is a separate, standing display unit. The up/down strike zone display unit 58 displays where from an up/down standpoint, the baseball hits in relation to the strike zone. The up/down strike zone display unit 58 may be a stand-alone display or a display on a computing device.

Figure 13:
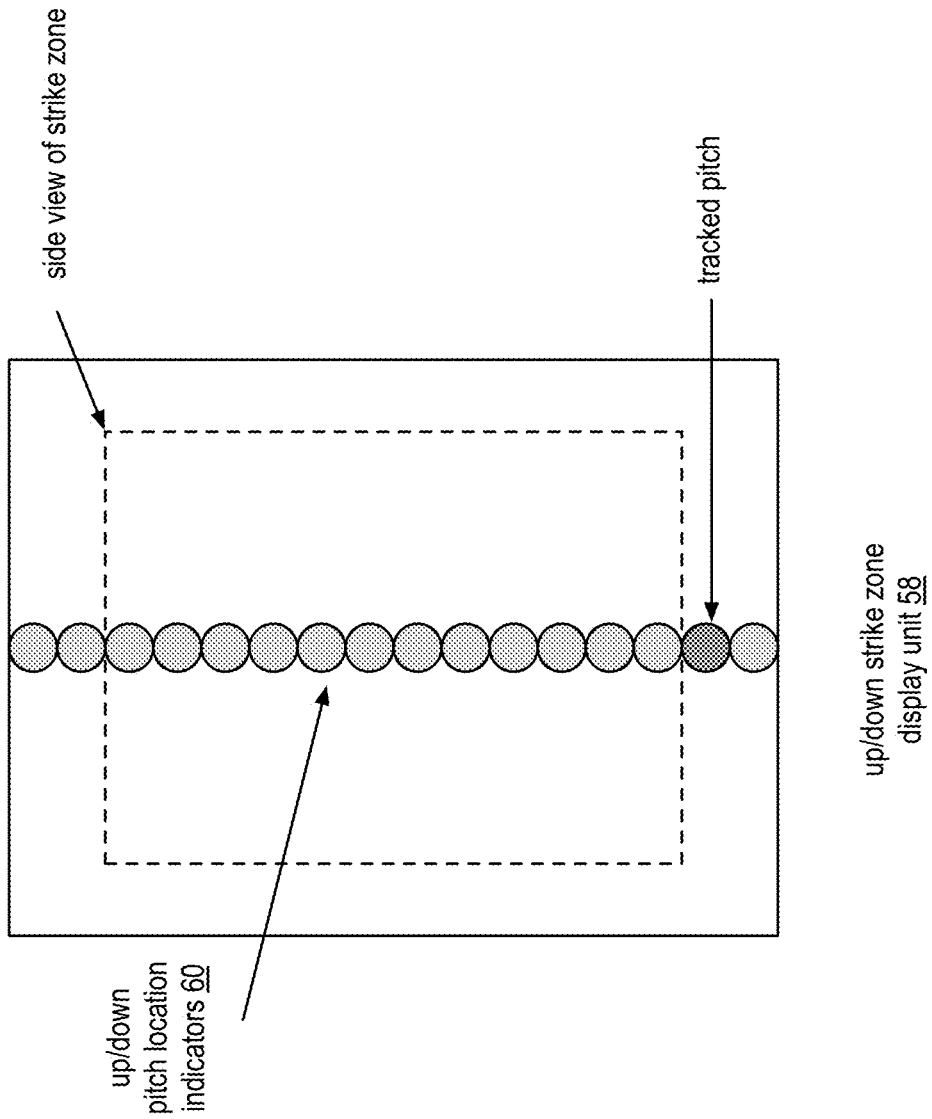
FIG. 13 is a diagram of another embodiment of a display unit of a local object detection system in accordance with the present invention.

FIG. 13 is another example of a display unit 58 of a local object detection system. FIG. 13 depicts an example display for the up/down strike zone display unit 58 of FIG. 12. The up/down strike zone display unit 58 includes up/down pitch location indicators 52 that run the length of the display. An indicator is illuminated (e.g., via LED) on the display unit 58 to identify the path of the baseball in relation to the strike zone. When a baseball is detected, located, and mapped by the processing module of the local object detection system, the processing module determines to illuminate one indicator that best represents the baseball's tracked path. For example, a baseball tracked going down the center of the up/down view of the strike zone will illuminate the center indicator (shown here as circular shapes to represent baseballs). A baseball that is pitched high and above the strike zone will illuminate one of the top indicators depending on which is the better representation.

Figure 14:
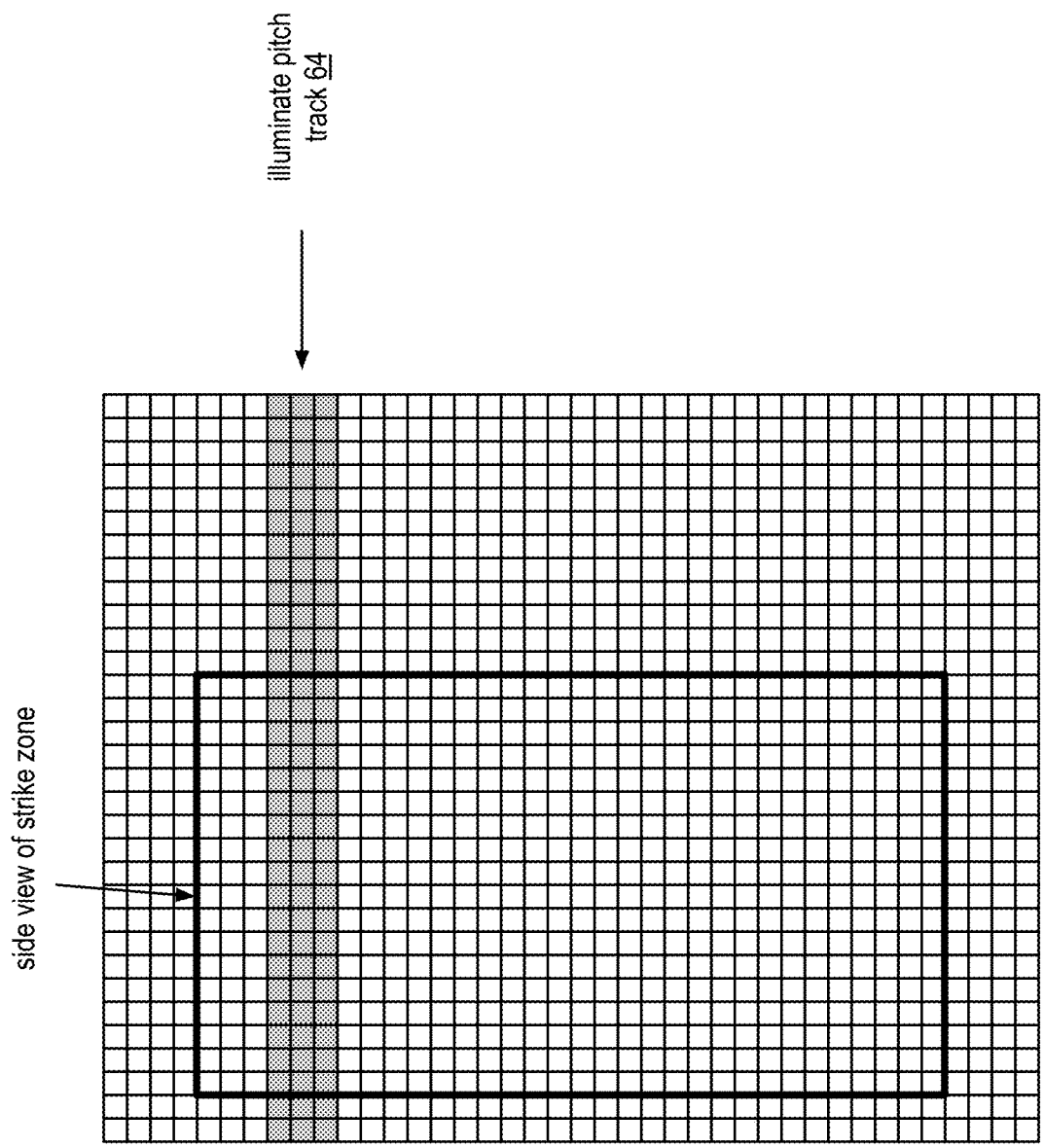
FIG. 14 is a diagram of another embodiment of a display unit of a local object detection system in accordance with the present invention.

FIG. 14 is another example of a display unit 62 of a local object detection system. The display unit shown is an up/down strike zone display unit similar to display unit 58 however the display unit in FIG. 14 includes a grid such that the entire display unit is capable of illumination. With the grid up/down strike zone display unit, the full path of a baseball can be mapped onto the grid up/down strike zone display unit 62. A pitch track 64 is illuminated (e.g., via LED) on the grid up/down strike zone display unit 62 to identify the path of the baseball in relation to the strike zone from an up/down point of view. When a baseball is detected, located, and mapped by the processing module of the local object detection system, the processing module communicates that path as an illuminated path approximately the width of the baseball. For example, a baseball tracked going towards the upper limit of the strike zone will illuminate a path similar to what is shown.

Figure 15:
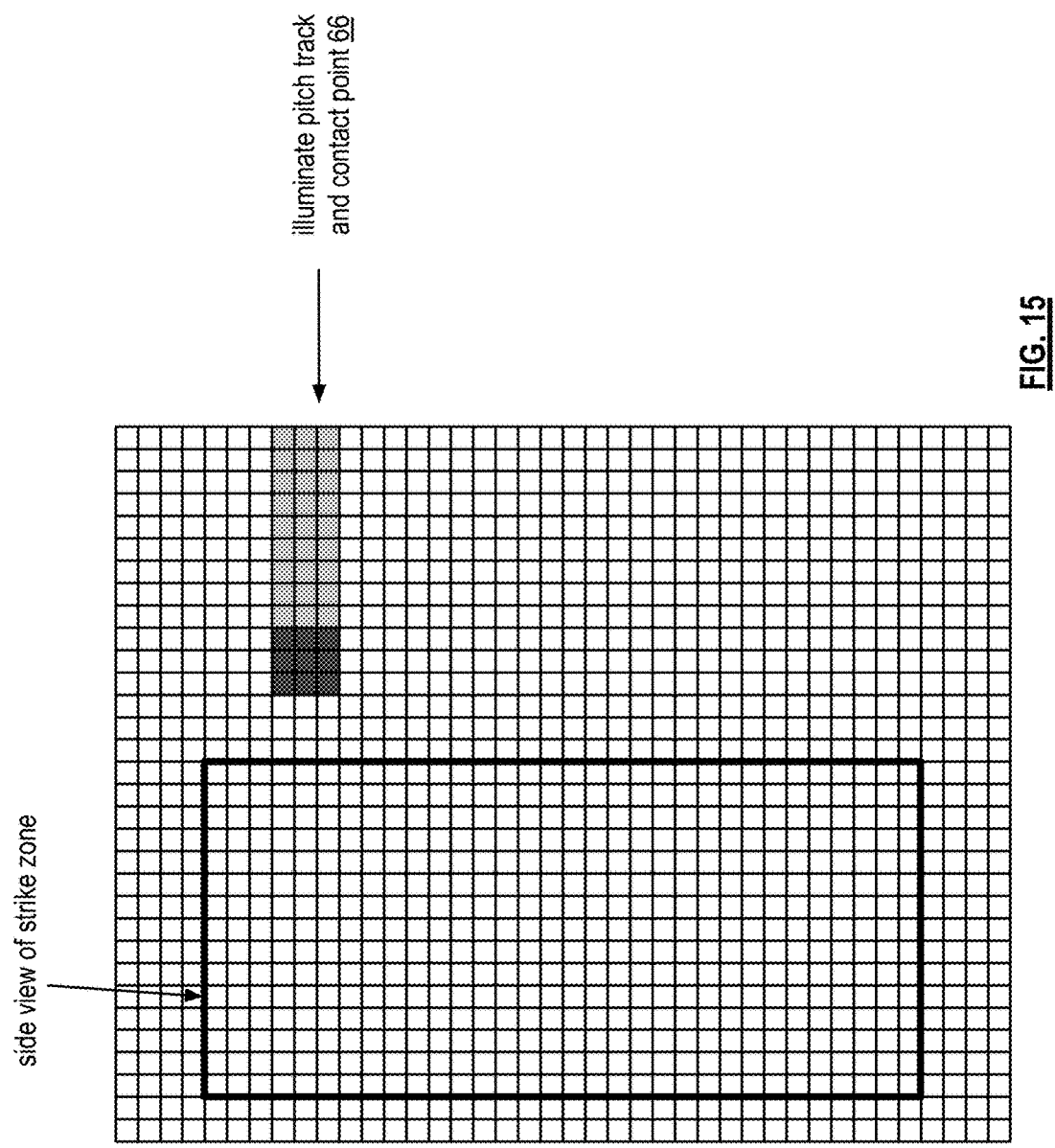
FIG. 15 is a diagram of another embodiment of a display unit of a local object detection system in accordance with the present invention.

FIG. 15 is another example of a display unit 62 of a local object detection system. The display unit shown is the up/down strike zone display unit 62 that is capable of displaying the pitch track of a baseball on the grid as well as a contact point 66. Instead of going through the hitting area and/or strike zone, a baseball may be hit by a bat cutting its path short. When a baseball is detected, located, and mapped by the processing module of the local object detection system, the processing module communicates that path as an illuminated path approximately the width of the baseball until that path in the pitch direction ends. The baseball bat is also tracked such that the point where the baseball and baseball bat collide is also mapped by the processing module and illuminated (e.g., by a different color LED illumination).

Figure 16:
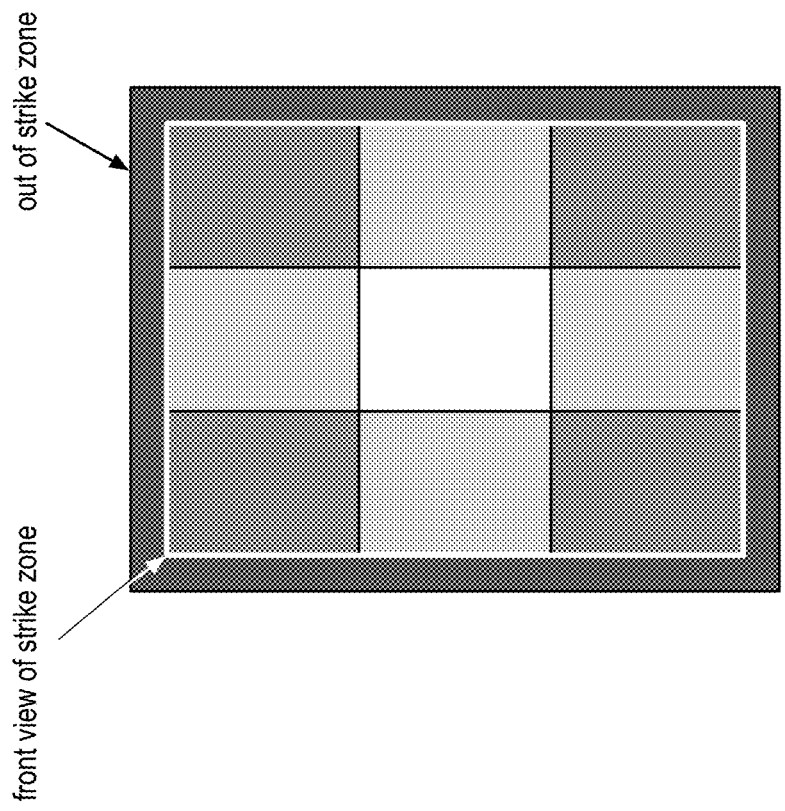
FIG. 16 is a diagram of another embodiment of a display unit of a local object detection system in accordance with the present invention.

FIG. 16 is another example of a display unit 68 of a local object detection system. FIG. 16 depicts an example display unit that combines the in/out grid display unit 54 and the grid up/down strike zone display unit 62. The in/out up/down strike zone display unit 68 includes a larger grid to indicate the location of the pitch (e.g., low and in, low and away, low and middle, mid and in, mid and away, mid and middle, high and in, high and away, and high and middle).

Figure 17:
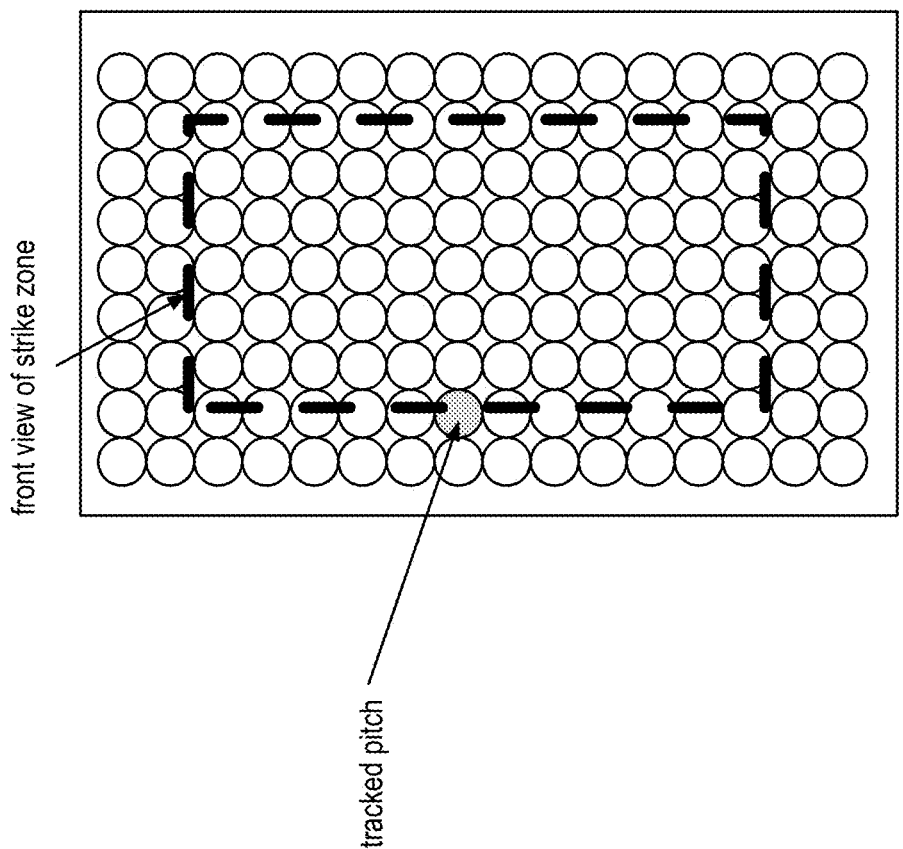
FIG. 17 is a diagram of another embodiment of a display unit of a local object detection system in accordance with the present invention.

FIG. 17 is another example of a display unit 70 of a local object detection system. FIG. 17 depicts an example display unit that combines the in/out display unit 50 and the up/down strike zone display unit 58. The in/out up/down strike zone display unit 68 includes both in/out and up/down pitch location indicators that cover the display unit. A path of indicators are illuminated (e.g., via LED) on the display unit 70 to identify the in/out and up/down path of the baseball in relation to the strike zone. When a baseball is detected, located, and mapped by the processing module of the local object detection system, the processing module determines to illuminate a line of indicators that best represents the baseball's in/out and up/down tracked path. For example, a baseball tracked going down the center of the in/out view will illuminate the vertical center line of indicators and a baseball tracked going down the center of the up/down view of the strike zone will illuminate the center horizontal line of indicators.

It is noted that terminologies as may be used herein such as bit stream, stream, signal sequence, etc. (or their equivalents) have been used interchangeably to describe digital information whose content corresponds to any of a number of desired types (e.g., data, video, speech, audio, etc. any of which may generally be referred to as 'data').

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A method comprises:
   transmitting, by a transmitter section of a local object detection system, one or more local transmit radar signals;
   receiving, by a plurality of receivers of the local object detection system, a plurality of local receive radar signals that corresponds to the one or more local transmit radar signals being reflected or refracted off an object;
   processing, by a processing module of the local object detection system, the plurality of local receive radar signals to determine a relative position of the object;
   determining, by the processing module, whether the object is positioned within a desired detection volume associated with a position of the transmitter section;
   when the object is positioned within the desired detection volume, further processing, by the processing module, the plurality of local receive radar signals to determine movement pattern of the object;
   determining, by the processing module, whether the movement pattern of the object is within a range of plausible movements for the object;
   when the movement pattern of the object is within a range of plausible movements for the object, tracking, by the processing module, movement of the object within the desired detection volume
   receiving, by at least some of the plurality of receivers, a second plurality of local receive radar signals that corresponds to the one or more local transmit radar signals being reflected or refracted off a second object;
   processing, by the processing module, the second plurality of local receive radar signals to determine a second relative position of the second object;

determining, by the processing module, whether the second object is positioned within the desired detection volume;

when the second object is positioned within the desired detection volume, further processing, by the processing module, the second plurality of local receive radar signals to determine second movement pattern of the second object;

determining, by the processing module, whether the second movement pattern of the second object is within a second range of plausible movements for the second object;

when the second movement pattern of the second object is within the second range of plausible movements for the second object, tracking, by the processing module, movement of the second object within the desired detection volume; and when the first object is a baseball and the second object is a bat, determining, by the processing module, a contact point of the bat colliding with the baseball based on the movements and positions of the baseball and the bat within the desired detection volume.

2. The method of claim 1, wherein a local transmit radar signal of the one or more local transmit radar signals comprises one of:
a radio frequency signal;
an infrared signal; and
an ultrasound signal.

3. The method of claim 1 further comprises:
the further processing of the plurality of local receive radar signals includes determining a relative velocity as part of the movement pattern; and
the determining whether the movement pattern of the object is within a range of plausible movements for the object further includes determining that the relative velocity is within an anticipated velocity range of the object.

4. The method of claim 1, wherein the processing the plurality of local receive radar signals to determine the relative position of the object comprises:
utilizing a triangulation location function of three or more of the plurality of local receive radar signals with respect to a reference point to determine the relative position.

5. The method of claim 1, wherein the desired detection volume comprises:
a three-dimensional space defined by a Cartesian coordinate system or a Polar coordinate system with respect to a reference point, wherein the reference point is based on location of the transmitter section.

6. The method of claim 1 further comprises:
when the first object is a first sensor on a wrist of a person's arm and the second object is a second sensor on an elbow of the person's arm, determining, by the processing module, movement of the person's arm based on movements and positions of the first sensor and the second sensor within the desired detection volume.

7. A computer readable memory comprises:
a first memory element that stores operational instructions that, when executed by a transmitter section of a local object detection system, causes the transmitter section to:
transmit one or more local transmit radar signals;

a second memory element that stores operational instructions that, when executed by a plurality of receivers of the local object detection system, cause the plurality of receivers to:
receive a plurality of local receive radar signals that corresponds to the one or more local transmit radar signals being reflected or refracted off an object; and
receive a second plurality of local receive radar signals that corresponds to the one or more local transmit radar signals being reflected or refracted off a second object;

a third memory element that stores operational instructions that, when executed by a processing module of the local object detection system, causes the processing module to:
process the plurality of local receive radar signals to determine a relative position of the object;
determining whether the object is positioned within a desired detection volume associated with a position of the transmitter section;
when the object is positioned within the desired detection volume, further process the plurality of local receive radar signals to determine movement pattern of the object;
determine whether the movement pattern of the object is within a range of plausible movements for the object;
when the movement pattern of the object is within a range of plausible movements for the object, track movement of the object within the desired detection volume;
process the second plurality of local receive radar signals to determine a second relative position of the second object;
determine whether the second object is positioned within the desired detection volume;
when the second object is positioned within the desired detection volume, further process the second plurality of local receive radar signals to determine second movement pattern of the second object;
determine whether the second movement pattern of the second object is within a second range of plausible movements for the second object; and
when the second movement pattern of the second object is within the second range of plausible movements for the second object, track movement of the second object within the desired detection volume;
when the first object is a baseball and the second object is a bat, determine a contact point of the bat colliding with the baseball based on the movements and positions of the baseball and the bat within the desired detection volume.

8. The computer readable memory of claim 7, wherein a local transmit radar signal of the one or more local transmit radar signals comprises one of:
a radio frequency signal;
an infrared signal; and
an ultrasound signal.

9. The computer readable memory of claim 7, wherein the third memory element further stores operational instructions that, when executed by the processing module, causes the processing module to:
further process the plurality of local receive radar signals to determine a relative velocity as part of the movement pattern; and
determine whether the movement pattern of the object is within a range of plausible movements for the object by determining that the relative velocity is within an anticipated velocity range of the object.

10. The computer readable memory of claim 7, wherein the third memory element further stores operational instructions that, when executed by the processing module, causes the processing module to process the plurality of local receive radar signals to determine the relative position of the object by:
   utilizing a triangulation location function of three or more of the plurality of local receive radar signals with respect to a reference point to determine the relative position.

11. The computer readable memory of claim 7, wherein the desired detection volume comprises:
   a three-dimensional space defined by a Cartesian coordinate system or a Polar coordinate system with respect to a reference point, wherein the reference point is based on location of the transmitter section.

12. The computer readable memory of claim 7 further comprises:
   the third memory element further stores operational instructions that, when executed by the processing module, causes the processing module to:
      when the first object is a first sensor on a wrist of a person's arm and the second object is a second sensor on an elbow of the person's arm, determine movement of the person's arm based on movements and positions of the first sensor and the second sensor within the desired detection volume.

* * * * *